(12) United States Patent
Daffinson et al.

(10) Patent No.: US 10,758,366 B2
(45) Date of Patent: *Sep. 1, 2020

(54) INTERVERTEBRAL IMPLANT DEVICE WITH INDEPENDENT DISTAL-PROXIMAL EXPANSION

(71) Applicant: Amendia, Inc., Marietta, GA (US)

(72) Inventors: Brion Daffinson, Marietta, GA (US); Austin Howell, Decatur, GA (US); Chase Thornburg, Cumming, GA (US)

( * ) Notice: Subject to any disclaimer, the term of this patent is extended or adjusted under 35 U.S.C. 154(b) by 74 days.

This patent is subject to a terminal disclaimer.

(21) Appl. No.: 15/645,575

(22) Filed: Jul. 10, 2017

(65) Prior Publication Data

US 2018/0147065 A1 May 31, 2018

Related U.S. Application Data

(63) Continuation of application No. 15/363,392, filed on Nov. 29, 2016, now Pat. No. 9,750,618.

(51) Int. Cl.
*A61F 2/44* (2006.01)
*A61F 2/30* (2006.01)

(52) U.S. Cl.
CPC .... *A61F 2/447* (2013.01); *A61F 2002/30266* (2013.01); *A61F 2002/30387* (2013.01); *A61F 2002/30405* (2013.01); *A61F 2002/30476* (2013.01); *A61F 2002/30507* (2013.01); *A61F 2002/30515* (2013.01); *A61F 2002/30538* (2013.01); *A61F 2002/30556* (2013.01); *A61F 2002/30578* (2013.01); *A61F 2002/30579* (2013.01); *A61F 2002/30593* (2013.01); *A61F 2220/0008* (2013.01)

(58) Field of Classification Search
CPC .................. A61F 2/447; A61F 2/4455; A61B 2017/4475; A61B 2017/30387
See application file for complete search history.

(56) References Cited

U.S. PATENT DOCUMENTS

| 196,117 A | 10/1877 | Greenleaf |
| 5,658,335 A | 8/1997 | Allen |
| 6,641,614 B1 | 11/2003 | Wagner et al. |
| 6,723,126 B1 | 4/2004 | Berry |
| 7,708,779 B2 | 5/2010 | Edie et al. |
| 7,854,766 B2 | 12/2010 | Moskowitz et al. |

(Continued)

FOREIGN PATENT DOCUMENTS

DE 102013113168 6/2015

*Primary Examiner* — Amy R Sipp

(57) ABSTRACT

An expandable interbody fusion implant device has a frame, two ramp assemblies and two overlying base plates driven by two independent drive shafts. The two ramp assemblies include a distal ramp assembly and a proximal ramp assembly. Each ramp assembly has a translating ramp, a first pivoting hinged ramp and a second pivoting hinged ramp. The two overlying base plates include a first base plate overlying a second base plate. Each base plate is hinged to the distal ramp assembly and the proximal ramp assembly at an end of one of said pivoting hinged ramps of each ramp assembly. The two independently driven drive shafts include a first drive shaft for translating the distal ramp assembly and a second drive shaft for translating the proximal ramp assembly to independently expand the implant proximally or distally or both.

10 Claims, 48 Drawing Sheets

(56) References Cited

U.S. PATENT DOCUMENTS

| | | |
|---|---|---|
| 8,231,681 B2 | 7/2012 | Castleman et al. |
| 8,257,442 B2 | 9/2012 | Edie et al. |
| 8,303,663 B2 | 11/2012 | Jumenez et al. |
| 8,579,979 B2 | 11/2013 | Edie et al. |
| 8,628,577 B1 | 1/2014 | Jimenez |
| 8,679,183 B2 | 3/2014 | Glerum et al. |
| 8,696,751 B2 | 4/2014 | Ashley et al. |
| 8,940,049 B1 | 1/2015 | Jimenez |
| 8,986,386 B2 | 3/2015 | Oglaza et al. |
| 9,078,769 B2 | 7/2015 | Farin |
| 9,358,125 B2 | 6/2016 | Jimenez et al. |
| 9,474,626 B2 | 10/2016 | Jimenez et al. |
| 2006/0253201 A1 | 11/2006 | McLuen |
| 2007/0270968 A1 | 11/2007 | Baynham |
| 2009/0210062 A1 | 8/2009 | Thalgott |
| 2015/0272743 A1* | 10/2015 | Jimenez .................. A61F 2/447 623/17.16 |
| 2016/0250034 A1* | 9/2016 | Loebl ........................ A61F 2/44 623/17.16 |
| 2016/0262907 A1 | 9/2016 | Jimenez |
| 2017/0172756 A1* | 6/2017 | Faulhaber ............. A61F 2/4425 |
| 2017/0333198 A1 | 11/2017 | Robinson |

* cited by examiner

INTERVERTEBRAL IMPLANT DEVICE WITH INDEPENDENT DISTAL-PROXIMAL EXPANSION

RELATED APPLICATIONS

The present invention is a continuation of U.S. application Ser. No. 15/363,392 filed on Nov. 29, 2016 entitled "Intervertebral Implant Device With Independent Distal-Proximal Expansion".

TECHNICAL FIELD

The present disclosure relates to an expandable interbody fusion implant device for implantation between vertebral bodies.

BACKGROUND OF THE INVENTION

Spinal stabilization can be achieved by providing an interbody implant. Some of these implants are bone, PEEK, solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to retain the implant in place.

It has been found desirable to keep the surgical opening as small as practical while still having sufficient room to insert the implant device and the end of an elongated tool or insertion instrument.

Advantageously, if the implant size could be reduced further that would allow the surgical opening to be reduced; however, once implanted the device needs to be expandable to provide sufficient spacing of the vertebrae.

A whole class of expandable interbody implant devices have been developed for this purpose. Some prior art devices use hydraulic expansion or inflatable balloons. Some devices are stackable elements piled on themselves to raise their height. Some use rotatable screw jack designs. Some are wedges that have a fixed hinged end and an opposite expandable end. All of the rotatable expandable devices using screw threads require the device to be round cylinders or posts.

One of the problems of such devices is the amount of post insertion manipulation required to reach a fully expanded properly space height is tedious and time consuming. Secondly, additional set screws or locking elements are often required to keep the device at its proper size. Thirdly, the devices of a circular shape are not the best fit for the adjacent vertebrae being spaced. Fourth, most of the devices have the internal space occupied with mechanisms limiting the amount of bone growth material available for packing the implants.

The wedge type implants generally contact the bone on an angle and expandable wedges when expanded simply expand on an angle not parallel to the vertebrae surface. This places localized high loading between the vertebrae because the wedge surfaces are not parallel to the vertebrae.

In some cases of vertebral misalignment, a controlled angulation of the implant device can be very beneficial to correct a pre-existing condition. Accordingly, in those cases having a wedge shape at a fixed angulation would mean the manufacturer would be required to make many devices with pre-set angles to select from. This simply is cost prohibitive.

Accordingly, the present invention provides a single device that can be expanded horizontally and parallel or, if preferred, can be expanded distally or proximally or both independently to allow the surgeon to choose the ideal orientation he wants to use to correct the spinal alignment.

These and other limitations in the prior art have been corrected and solved by the present invention as disclosed herein.

SUMMARY OF THE INVENTION

An expandable interbody fusion implant device has a frame, two ramp assemblies and two overlying base plates driven by two independent drive shafts. The frame has a distal end and a proximal end. The two ramp assemblies include a distal ramp assembly and a proximal ramp assembly. Each ramp assembly has a translating ramp, a first pivoting hinged ramp and a second pivoting hinged ramp. The two overlying base plates disposed between the distal end and the proximal end of the frame include a first base plate overlying a second base plate. Each base plate is hinged to the distal ramp assembly and the proximal ramp assembly at an end of one of said pivoting hinged ramps of each ramp assembly. The two independently driven drive shafts include a first drive shaft for translating the distal ramp assembly and a second drive shaft for translating the proximal ramp assembly. Each drive shaft is affixed to the frame at the distal and proximal ends.

Rotation of the first drive shaft can independently drive the distal ramp assembly to selectively expand or contract a distance between the two base plates distally and rotation of the second drive shaft can independently drive the proximal ramp assembly to selectively expand or contract a distance between the two base plates proximally. Sequential or simultaneous rotation of both first and second drive shafts independently drives the distal and proximal ramps to selectively expand or contract a distance between both first and second base plates to a selected inclination of the first and second base plates relative to the frame over a range of angles.

Each translating ramp has an exterior lift surface contoured to guide and support the pivoting hinged ramps during expansion or contraction of the base plates. During distal expansion of the base plates the translating ramp of the distal ramp assembly moves directionally toward the distal end of the frame on rotation of the first drive shaft. During proximal expansion of the base plates the translating ramp of the proximal ramp assembly moves directionally toward the proximal end of the frame on rotation of the second drive shaft. Each translating ramp has a stop wall configured to stop the pivoting hinged ramps at a full expansion height on both the distal and proximal ramp assemblies. Each pivoting hinged ramp has a contoured support surface configured to slide on the exterior lift surface of the translating ramp, wherein each pivoting hinged ramp contoured support surface is complimentary to the exterior lift surface. The contoured lift surface has a convex curvature; and the contoured support surface has a concave curvature of similar profile to fit onto a portion of the lift surface. The lift surface curvature of each translating ramp has a radius of curvature of decreasing inclination toward a center of the frame of the device and of increasing inclination toward ends of the frame configured to initially rapidly expand or contract near a collapsed or retracted position and a slower expansion or contraction near a fully expanded position. Each translating ramp has a pair of opposing sides, each side has a pair of guide channels or grooves, one for receiving and guiding one of the pivoting hinged ramps, each pivoting hinged ramp has a lateral side keyed into the guide channel or groove wherein each guide channel or groove extends toward an end forming the stop wall to limit the expansion of the pivoting hinged ramp.

Preferably, the distal end of the frame has a tapered end configured to facilitate insertion between vertebral bodies. The proximal end of the frame has a first opening and a second opening for receiving the first and second drive shafts, respectively, and further has lateral sides with slotted channels to receive a pin fixed to the proximal end of each of the first and second base plates. The pins configured to allow the base plates to slide relative to the proximal end of the frame during expansion or contraction.

Preferably, the base plates have an outer surface having a convex curvature with a crown or peak at the longitudinal midline of the implant that decreases as the curvature extends toward the distal or proximal end. The convex curvature is configured to mimic the end plate of the adjacent vertebra it supports and beneficially provides a large bearing surface regardless of the angulation of the base plates.

In a preferred embodiment, the first and second base plates as an optional feature each have, at the proximal end, an end plate with a fastener opening for securing the implant to a vertebral body. Each end plate is integral to and selectively movable with the base plate during expansion or contraction. Each end plate further has a locking tab attached to the end plate, the locking tab being rotatable to cover a portion of the fastener to prevent loosening after being affixed to a vertebral body. These end plates, when incorporated into the base plates, make the implant device of the present invention a unique standalone device.

In another alternative embodiment, the implant may only have one base plate, the first or the second base plate and the frame. In that embodiment, an expandable interbody fusion implant device would have a frame having a distal end and a proximal end, two ramp assemblies, one being a distal ramp assembly and the other a proximal ramp assembly, each ramp assembly has a translating ramp and at least one pivoting hinged ramp, at least one base plate disposed between the distal end and the proximal end of the frame, the at least one base plate overlying the frame, the at least one base plate being hinged to the distal ramp assembly and the proximal ramp assembly at an end of one of said at least one pivoting hinged ramp of each ramp assembly, two independently driven drive shafts, a first drive shaft for translating the distal ramp assembly and a second drive shaft for translating the proximal ramp assembly, each drive shaft being affixed to the frame at the distal and proximal ends, and wherein rotation of the first drive shaft can independently drive the distal ramp assembly to selectively expand or contract a distance between the at least one base plate distally, rotation of the second drive shaft can independently drive the proximal ramp assembly to selectively expand or contract a distance between the at least one base plate and the frame proximally and sequential or simultaneous rotation of both first and second drive shafts independently drives the distal and proximal ramps to selectively expand or contract a distance between the at least one base plate and the frame to a selected inclination of the at least one base plate relative to the frame over a range of angles. In this alternative, all the other features are the same as the preferred embodiment.

BRIEF DESCRIPTION OF THE DRAWINGS

The invention will be described by way of example and with reference to the accompanying drawings in which.

DETAILED DESCRIPTION OF THE INVENTION

Figure 1:
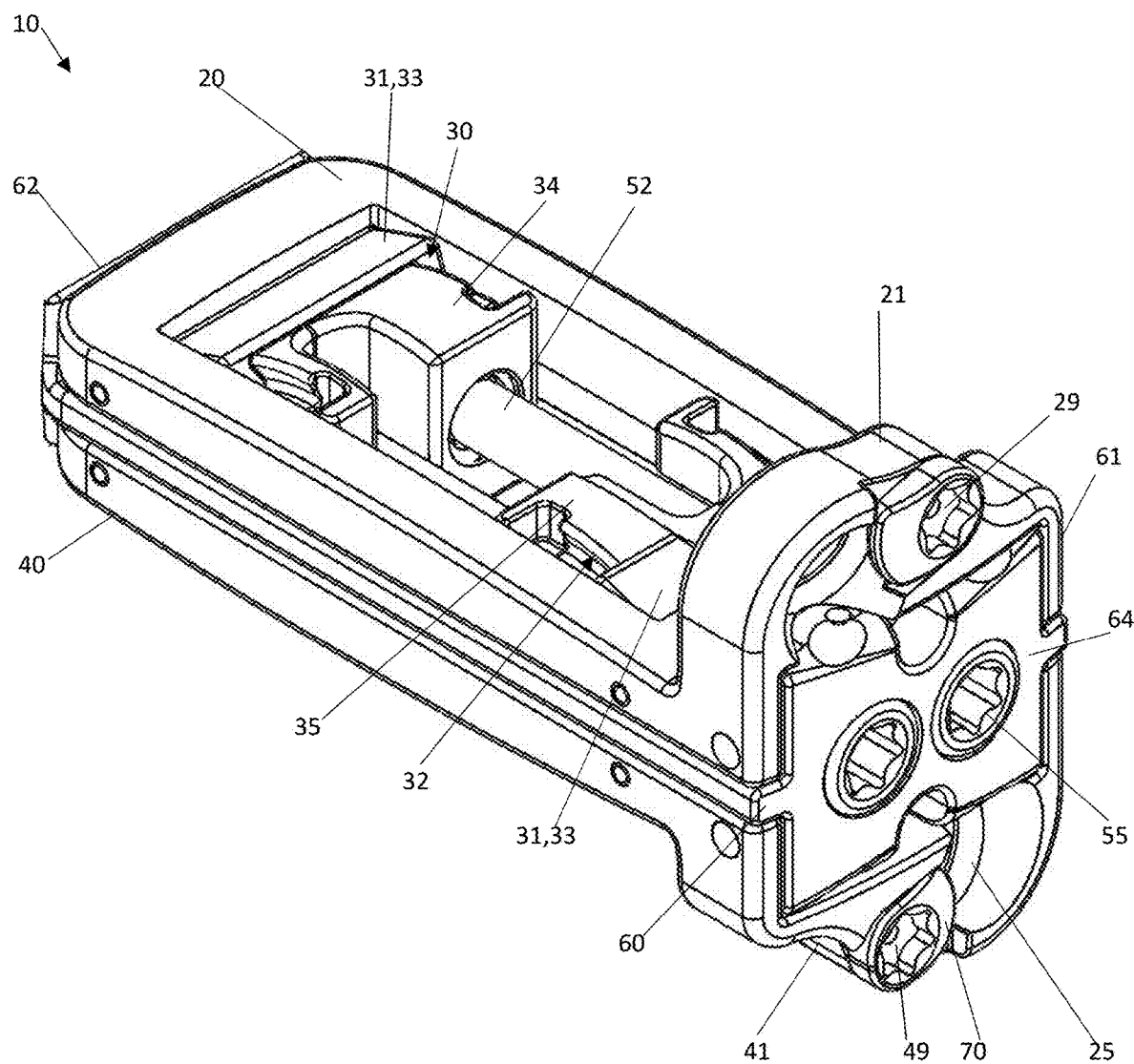
FIG. 1 is a perspective view of the expandable implant device of a preferred embodiment made in accordance with the present invention shown in a contracted non-expanded position.

The intervertebral implant device with independent distal-proximal expansion of the present invention, hereinafter described as an expandable interbody fusion implant device 10, has a frame 60, two ramp assemblies, 30, 32 and two overlying base plates 20, 40 driven by two independent drive shafts 50, 52; as illustrated in FIG. 1.

Figure 2:
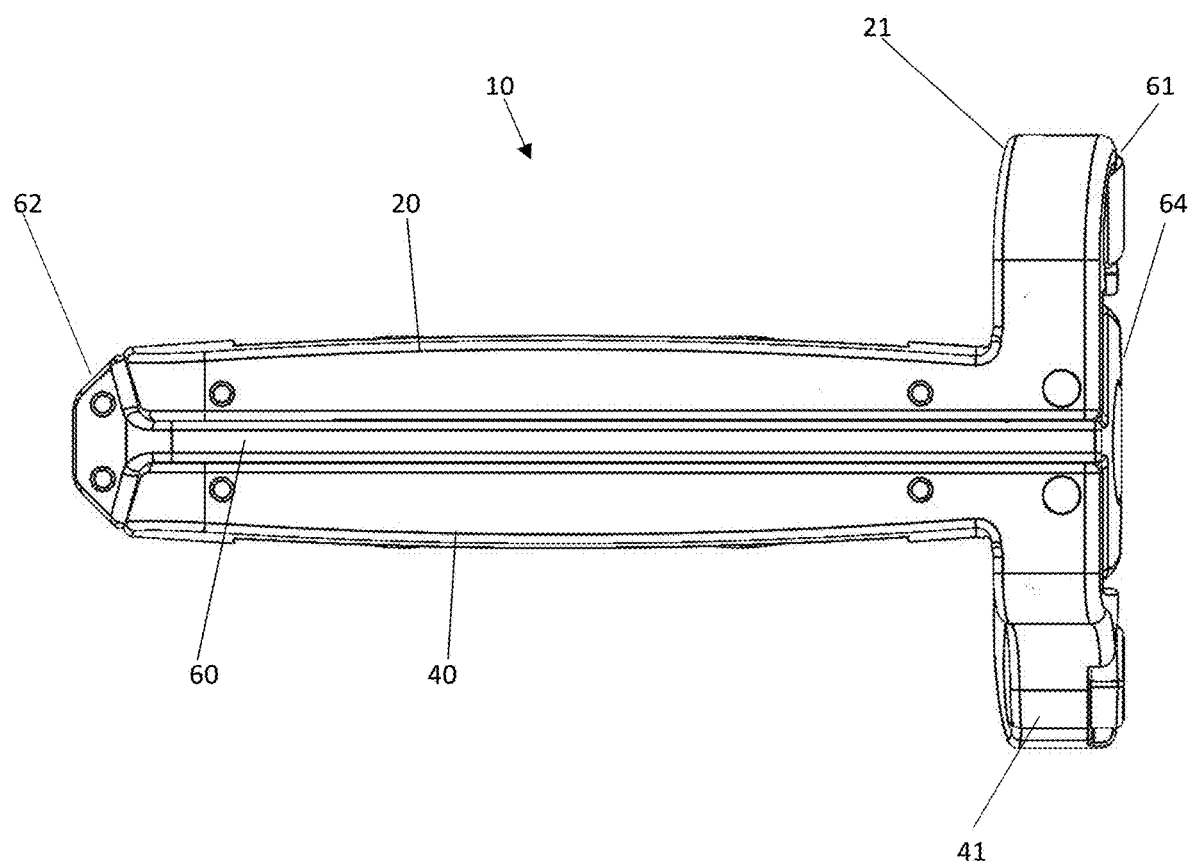
FIG. 2 is a side view of the expandable implant device taken from FIG. 1.

With reference to FIGS. 1 and 2, the device 10 shows the frame 60 having a distal end 62 and a proximal end 61. The two ramp assemblies 30, 32 include a distal translating ramp 34 and a proximal translating ramp 35 respectively, and further have a first pivoting hinged ramp 31 and a second pivoting hinged ramp 33. The two overlying base plates 20, 40 are disposed between the distal end 62 and the proximal end 61. The first base plate 20 overlies the second base plate 40. Each base plate 20, 40 is hinged to a distal ramp assembly 30 and the proximal ramp assembly 32 at an end of one of the said pivoting hinged ramps of each ramp assembly. The two independently driven drive shafts 50, 52 include a first drive shaft 50 for translating the distal ramp assembly 30 and a second drive shaft 52 for translating the proximal ramp assembly 32. Each drive shaft 50, 52 is affixed to the frame 60 at the distal and proximal end.

As shown in FIGS. 1 and 2, the implant device 10 is shown in a fully contracted position, this position is most suitable for insertion as it provides the lowest height between the opposing base plates 20, 40. As shown, the distal end 62 has a chamfered leading end surface further reducing the cross section as it enters between the intervertebral spaces providing a nice leading nose end for insertion. At the proximal end of the implant device 10, each base plate 20, 40 respectively have end plates 21 and 41. These end plates each are provided with a through hole 25 for receiving a threaded fastener 100. Threaded fastener 100 is shown in FIG. 3C.

Figure 3A:
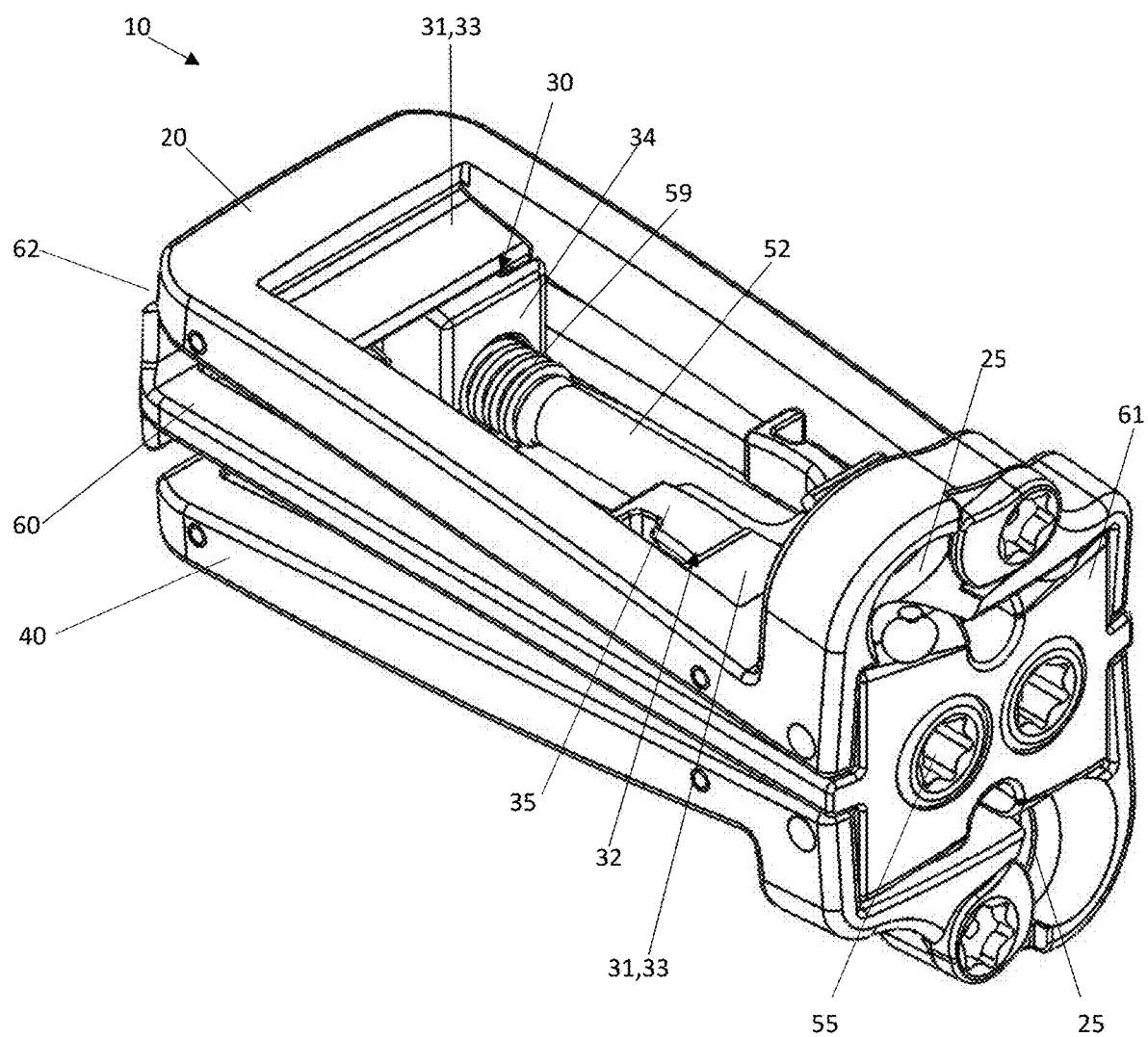
FIG. 3A is a perspective view of the device of FIG. 1 shown with the distal end expanded and the proximal end contracted.
Figure 3B:
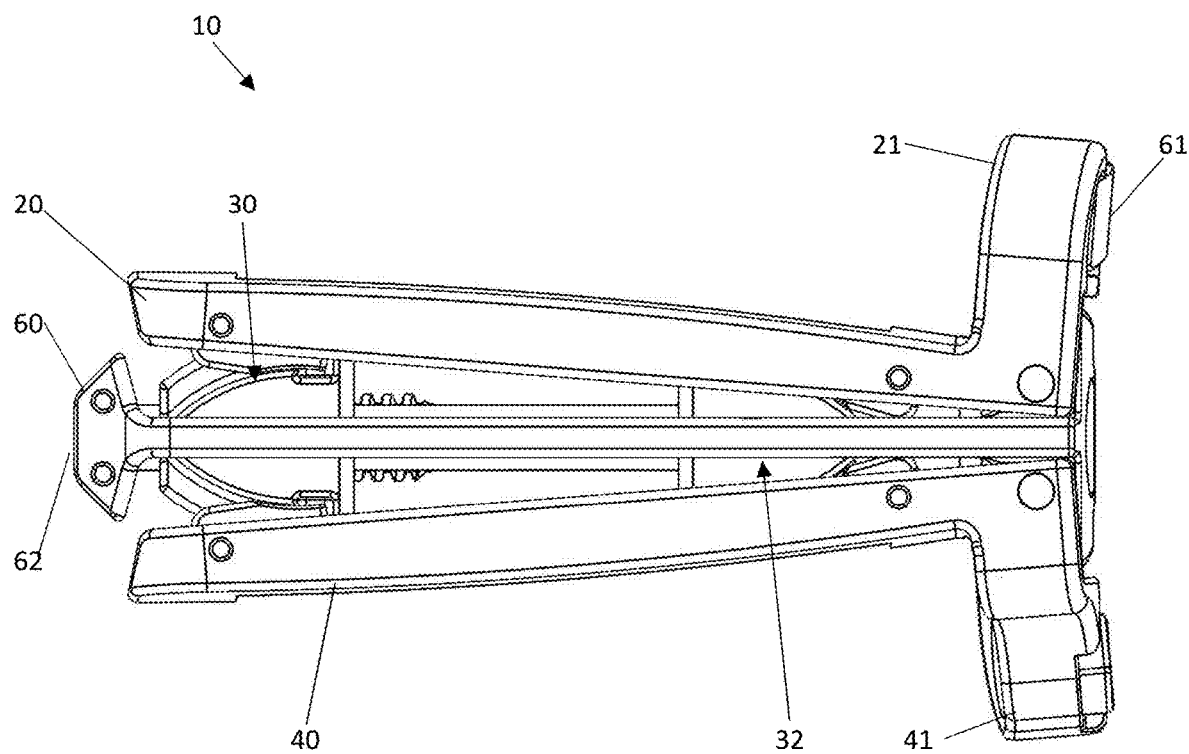
FIG. 3B is a side view taken from FIG. 3A.
Figure 3C:
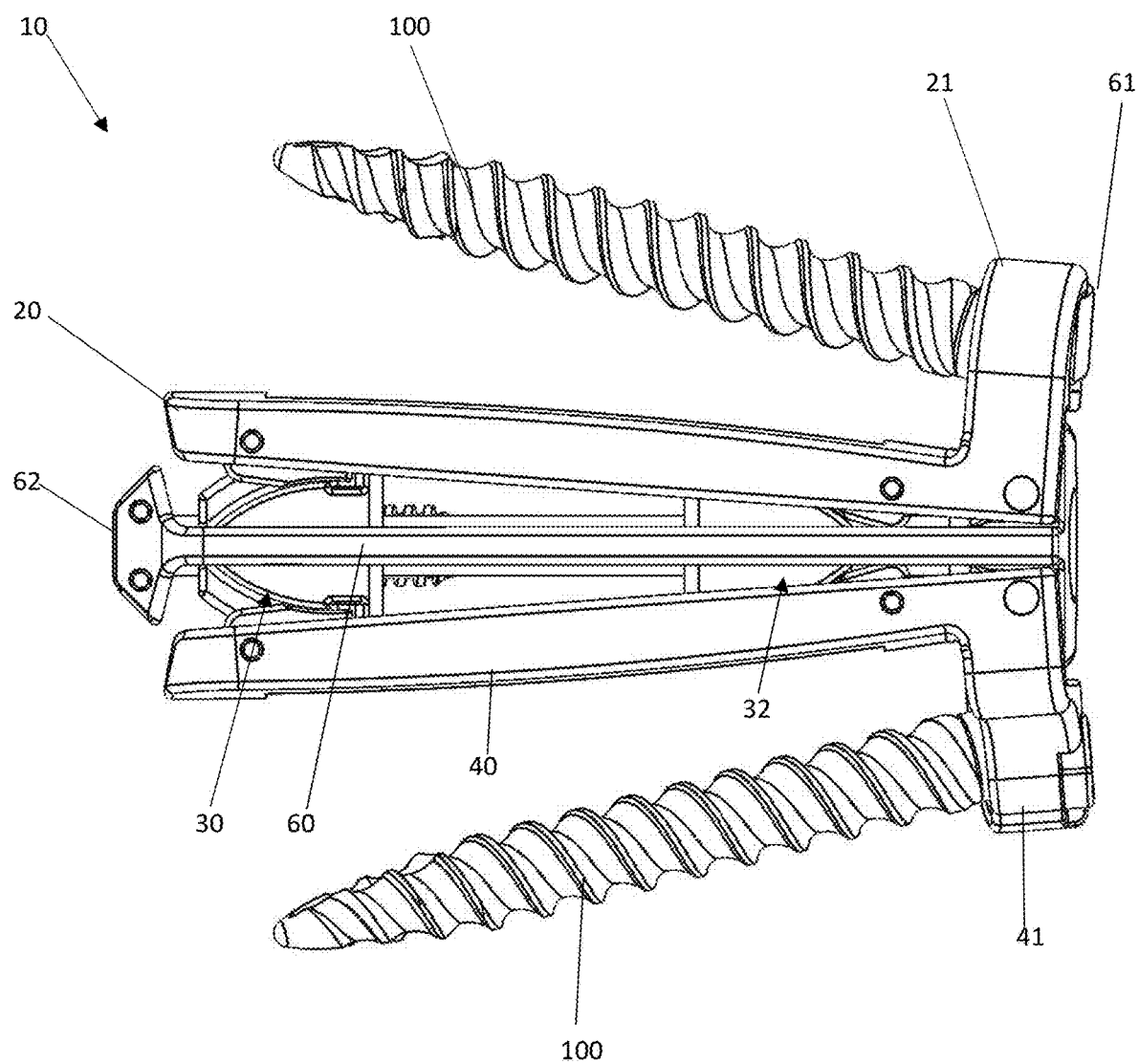
FIG. 3C is the side view taken from FIG. 3B with threaded fasteners installed in the proximal end of each first and second base plate.

With reference to FIGS. 3A-3C, the implant device 10 is shown where the first drive shaft 50 has been rotated such that the distal ramp assembly 30 is moved towards the distal end of the frame 62. When this occurs the translating ramp 34 of the distal ramp assembly 30 moves the pivoting hinged ramp 31 and 33 along an outer surface of the translating ramp 34 following the contour of the outer surface. When this drive shaft 50 is rotationally driven to rotate the distal end the base plates 20, 40 both are increased in height from the contracted state to an expanded state. This increase in height can occur in small increments anywhere dependent on the amount of the rotation of the drive shaft 50 and this rotation achieves a maximum level when the pivoting hinged ramp hits a stop wall 36 on the translating ramp 34. In the fully expanded condition, the distal end is shown elevated relative to the proximal end. This can best be seen in FIG. 3B from a side view. Threaded fasteners 100 can be inserted through the through holes 25 in both the first end plate 21 and the second end plate 41 of the first base plate 20 and the second base plate 40 respectively at any stage/position.

Figure 4A:
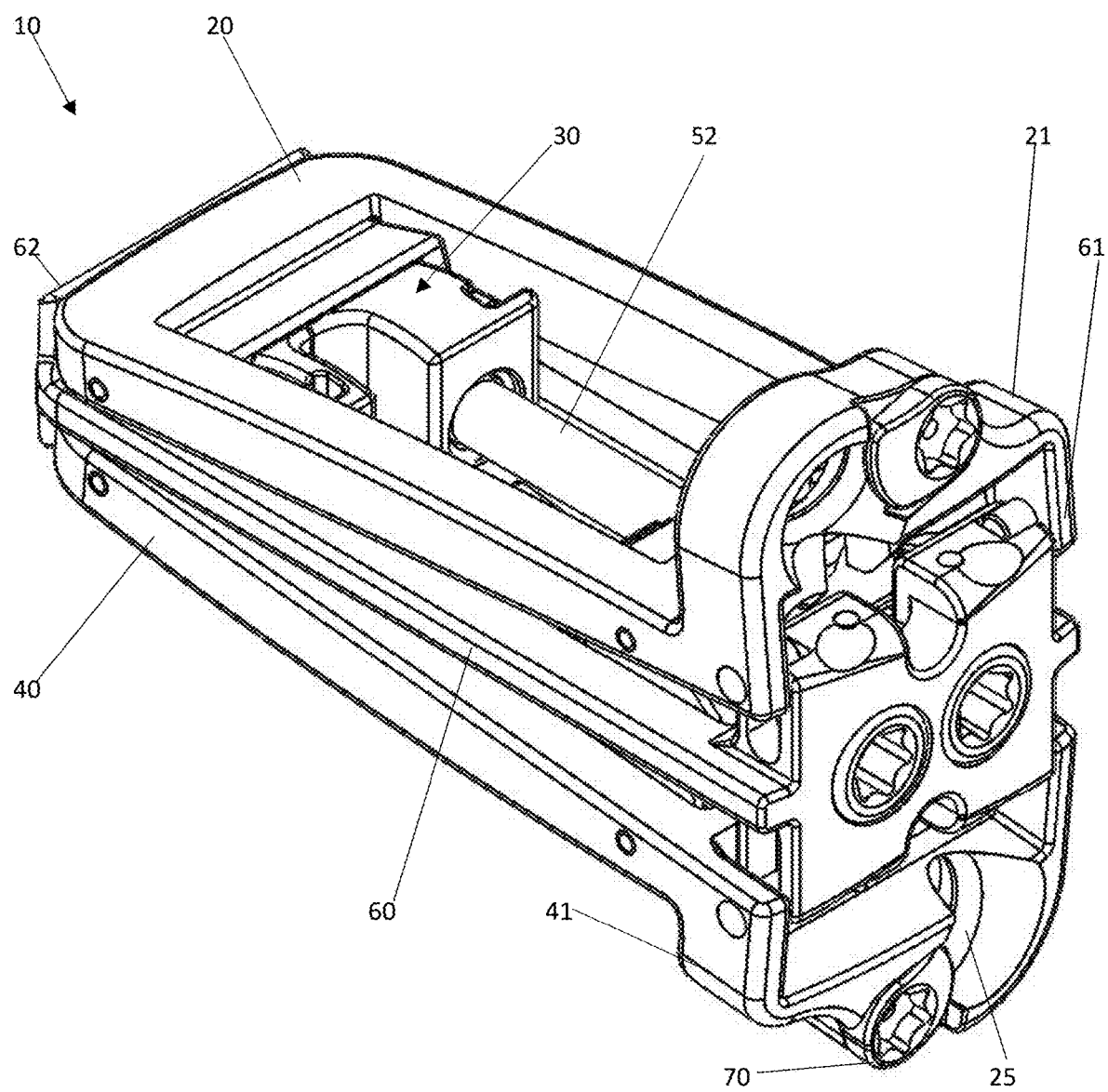
FIG. 4A is a perspective view of the device of FIG. 1 shown with the proximal end expanded and the distal end contracted.
Figure 4B:
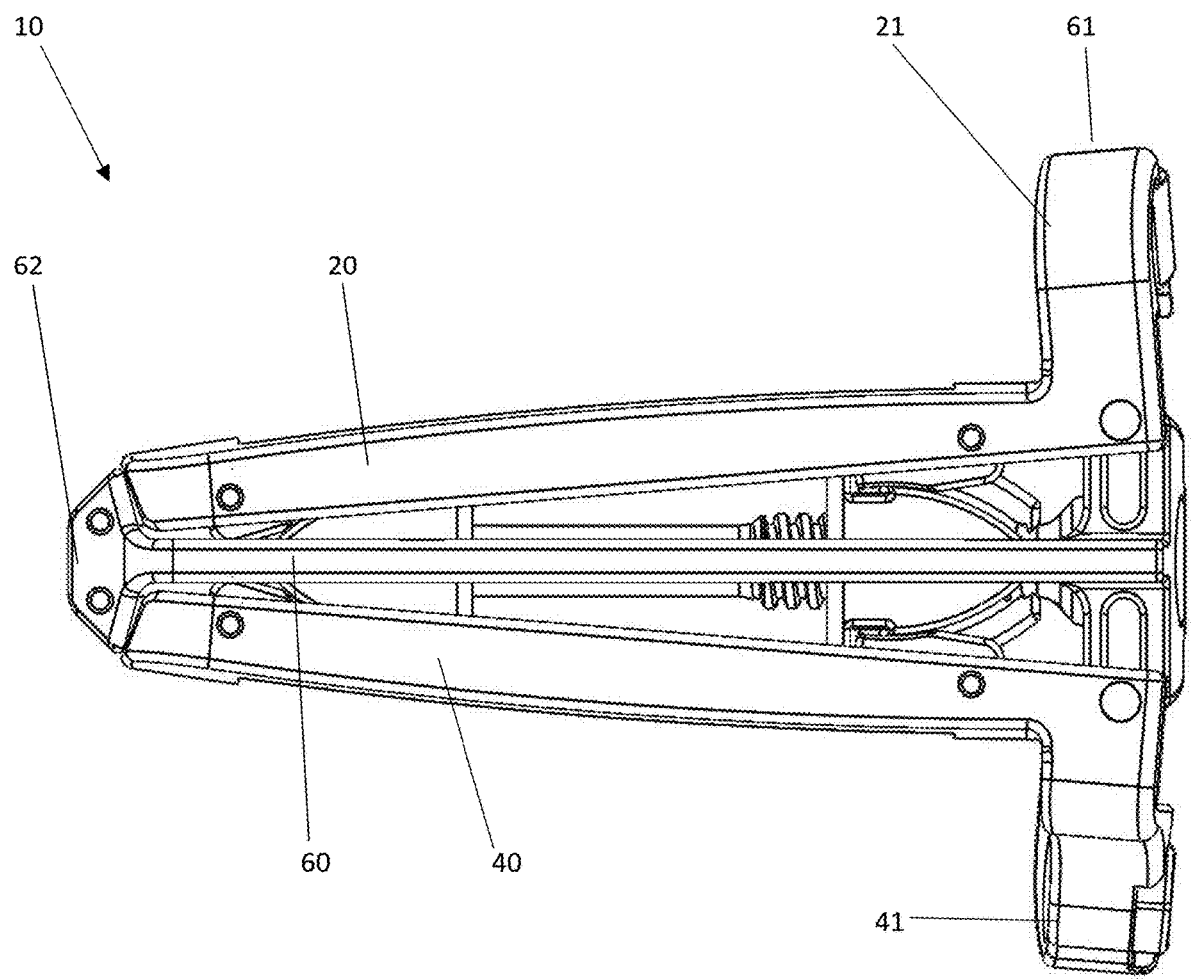
FIG. 4B is a side view taken from FIG. 4A.
Figure 4C:
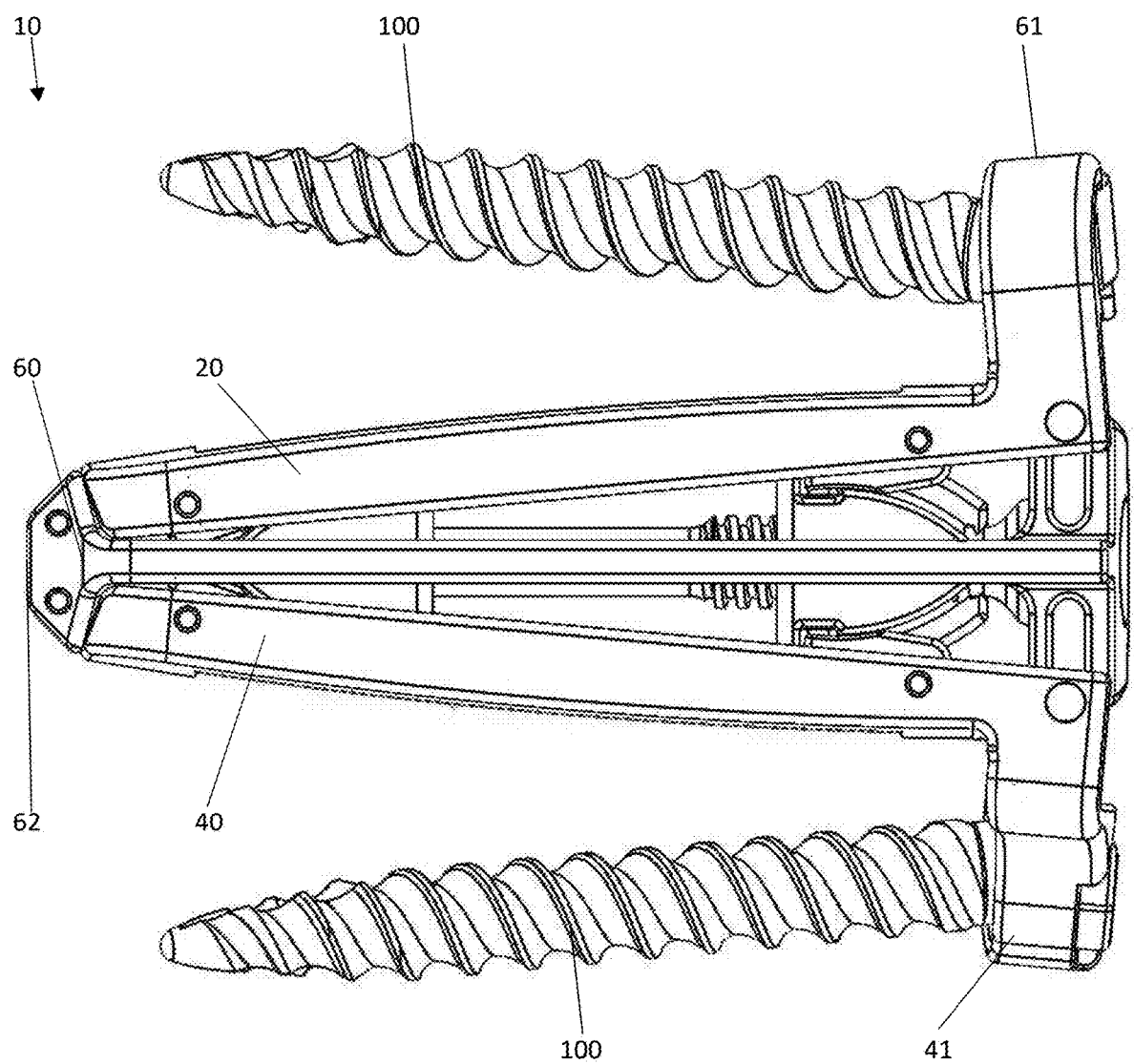
FIG. 4C is a side view taken from FIG. 4B with threaded fasteners installed in the proximal end of each first and second base plate.

With reference to FIG. 4A-4C, the implant device 10 alternatively, can have the second drive shaft 52 rotated in such a fashion that the proximal end 61 of the implant 10 will be elevated from a contracted position shown in FIG. 1 to the expanded position as shown in FIGS. 4A-4C. When this occurs, the translating ramp 35 of the proximal ramp assembly 32 is drawn toward the proximal end 61 of the frame 60 and as this occurs the pivoting hinged ramps 31, 33 ride on the outer surface of the ramp 35 such that the first base plate 20 and the second base plate 40 are moved increasing in height at the proximal end 61 as illustrated. This occurs independent of the distal end of the implant 10 as the distal end has not moved and is in the contracted position as illustrated in this embodiment. This feature allows the surgeon the option to move the implant 10 near the distal end 62 into an expanded condition or, alternatively, near the proximal end 61 into an expanded position or can move each end of the implant 10 by whatever increment or amount the surgeon prefers to set a desired angular inclination between the opposing base plate 20, 40 surfaces.

Figure 5A:
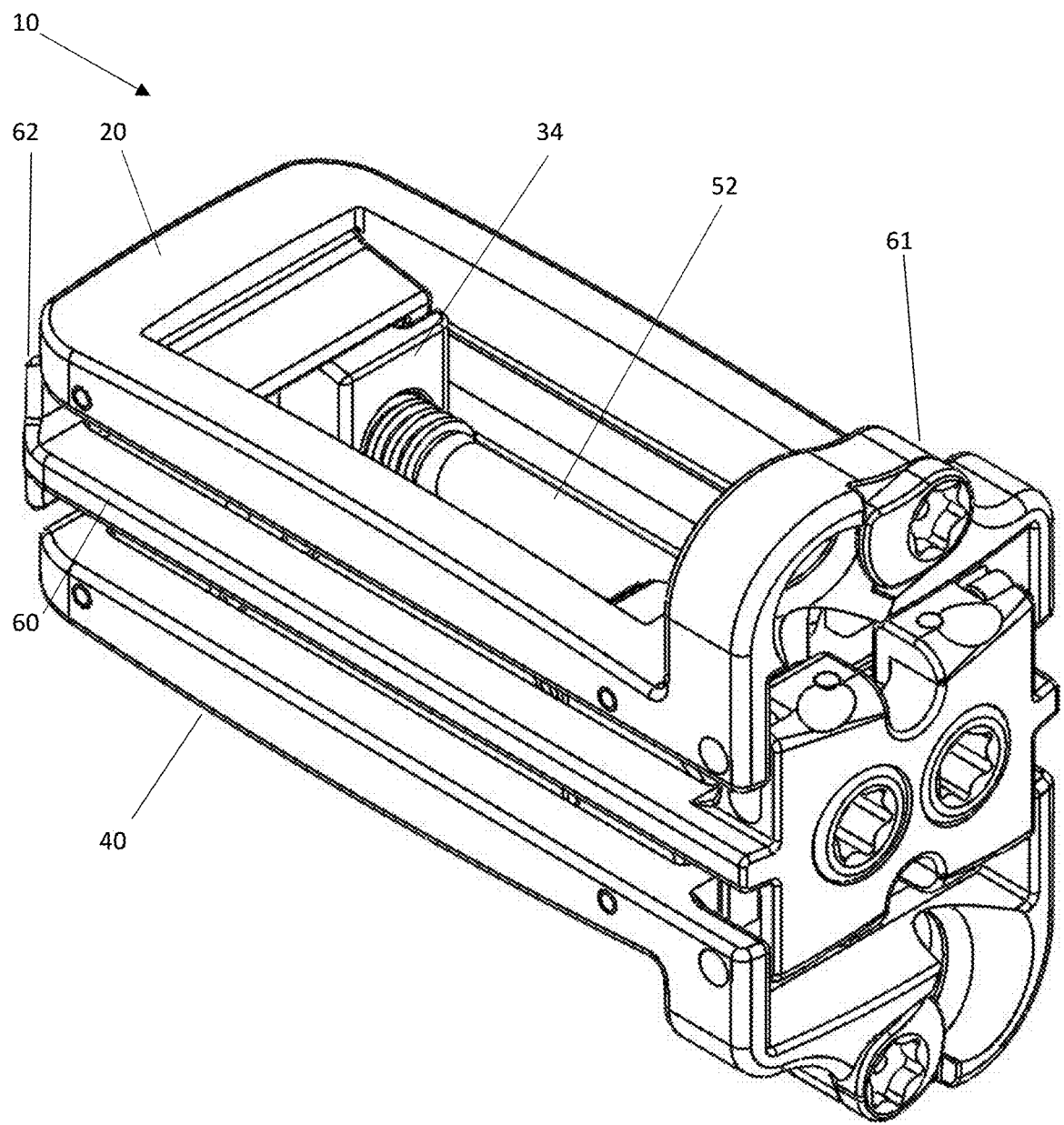
FIG. 5A is a perspective view of the device of FIG. 1 shown with the distal and the proximal end fully expanded.
Figure 5B:
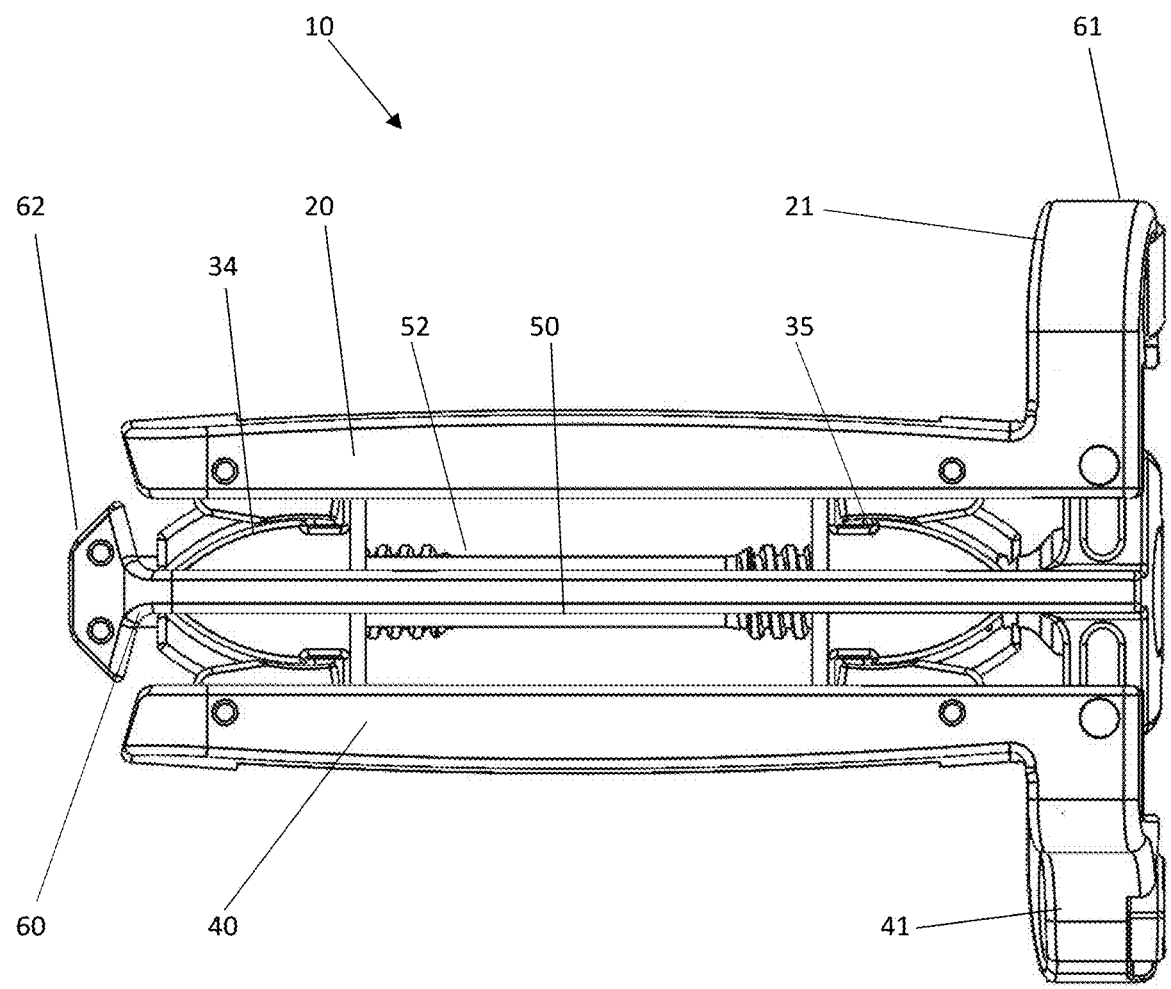
FIG. 5B is a side view of the device taken from FIG. 5A.
Figure 5C:
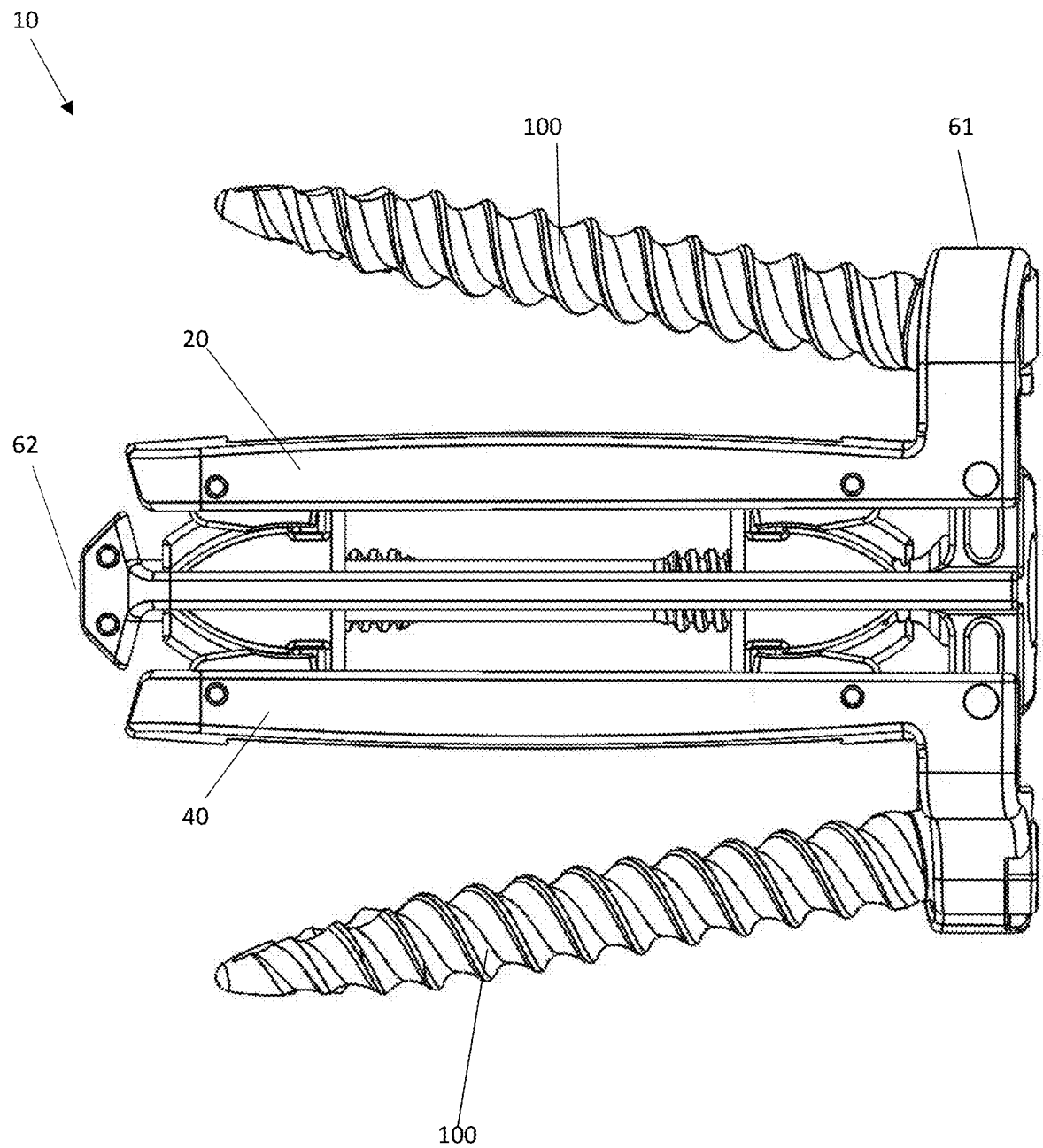
FIG. 5C is a side view taken from FIG. 5B with threaded fasteners installed in the proximal end of each first and second base plate.
Figure 5D:
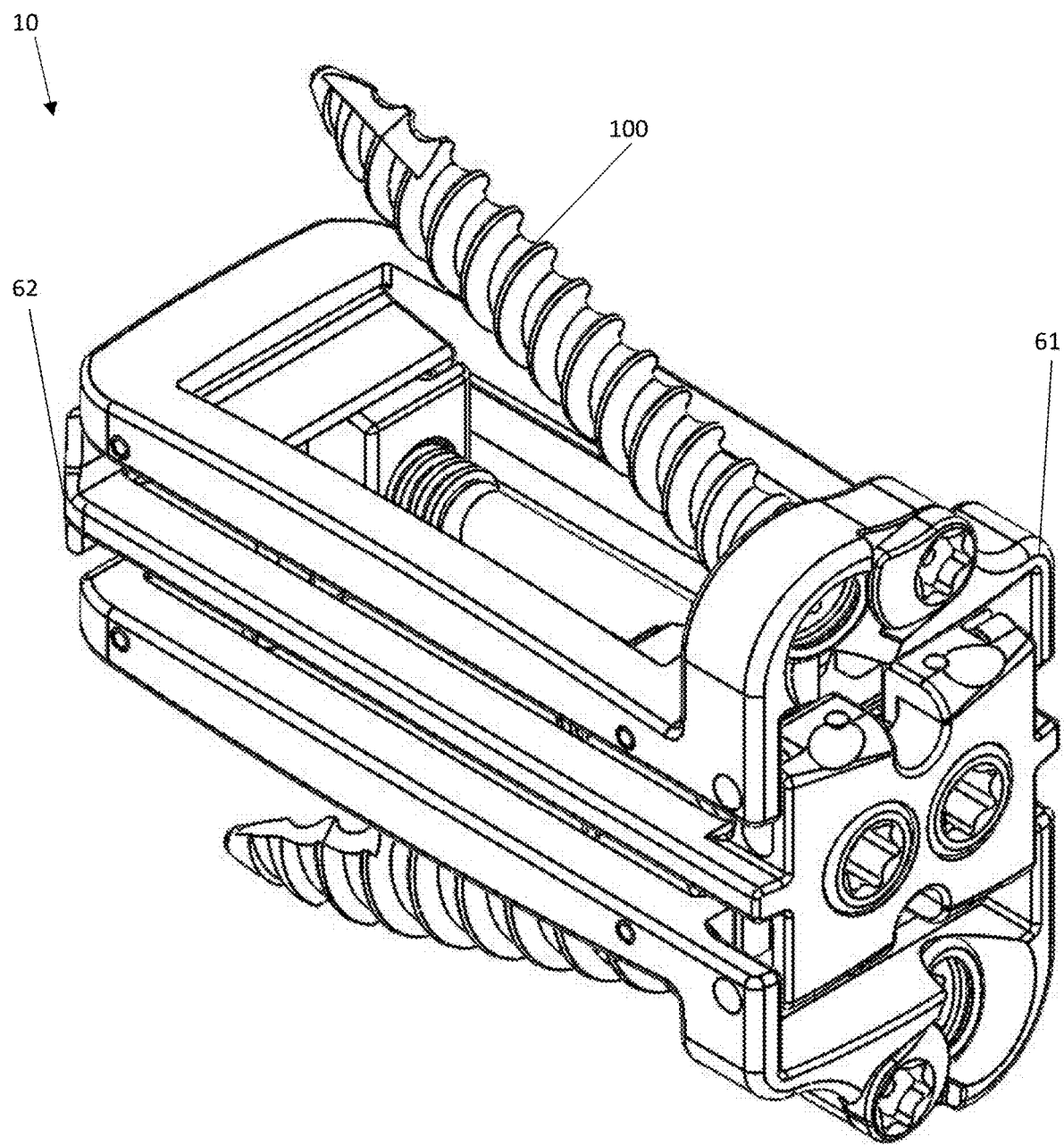
FIG. 5D is a perspective view of the device of FIG. 5A with threaded fasteners installed in the proximal end of each first and second base plate.

With reference to FIGS. 5A-5C, the implant device 10 is shown where both the first drive shaft 50 and the second drive shaft 52 have been rotated into a fully expanded position. When this occurs, the first base plate 20 moves outwardly both distally and proximally as does the second base plate 40 move both distally and proximally. Both base plates 20, 40 will move equally as they are driven by the translating ramp 34 at the distal ramp assembly 30 and the translating ramp 35 of the proximal ramp assembly 32 assuming that the contours on both ramps 34, 35 are made identical in surface contour and elevation. When both drive shafts 50, 52 are turned in this position, the base plates 20, 40 are moved relatively horizontal and parallel to each other which is more conventional to a common expandable implant device. However, a unique feature is that this expansion can be independently adjusted proximally and distally to achieve this position. One drive shaft 50 or 52 can be rotated more or one less to create any desired inclination between a range of maximum full expansion and partially expanded and anywhere in between based on the rotational selection chosen for each drive shaft 50, 52 by the surgeon.

Figure 6A:
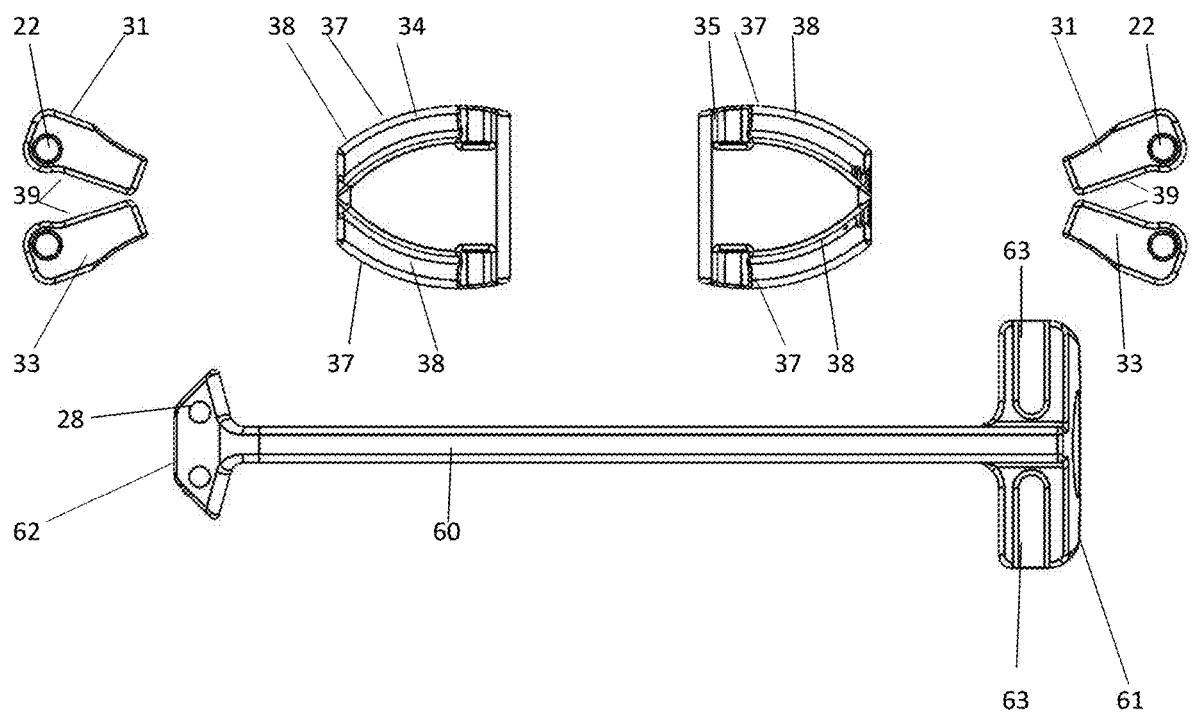
FIG. 6A is an exploded side view of the frame and ramp assemblies of the present invention as a first assembly step.
Figure 6B:
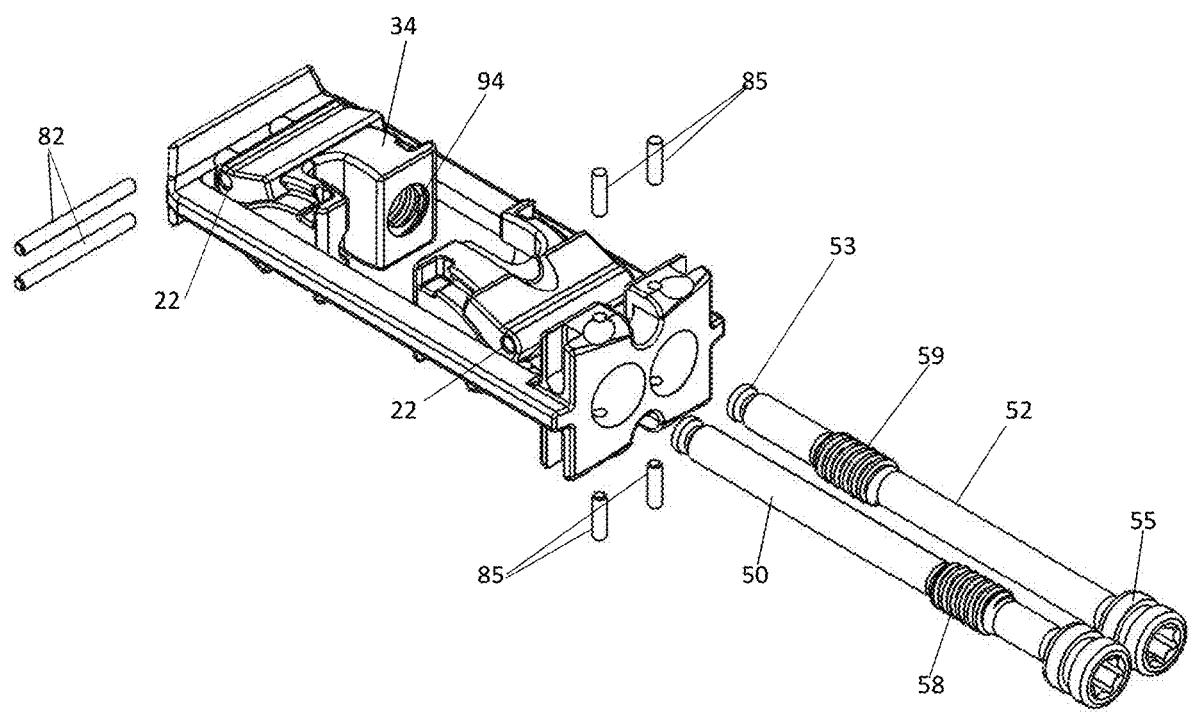
FIG. 6B is a perspective view of the assembled frame and ramp assemblies of FIG. 6A with the drive shafts and pins shown exploded as a second assembly step.
Figure 6C:
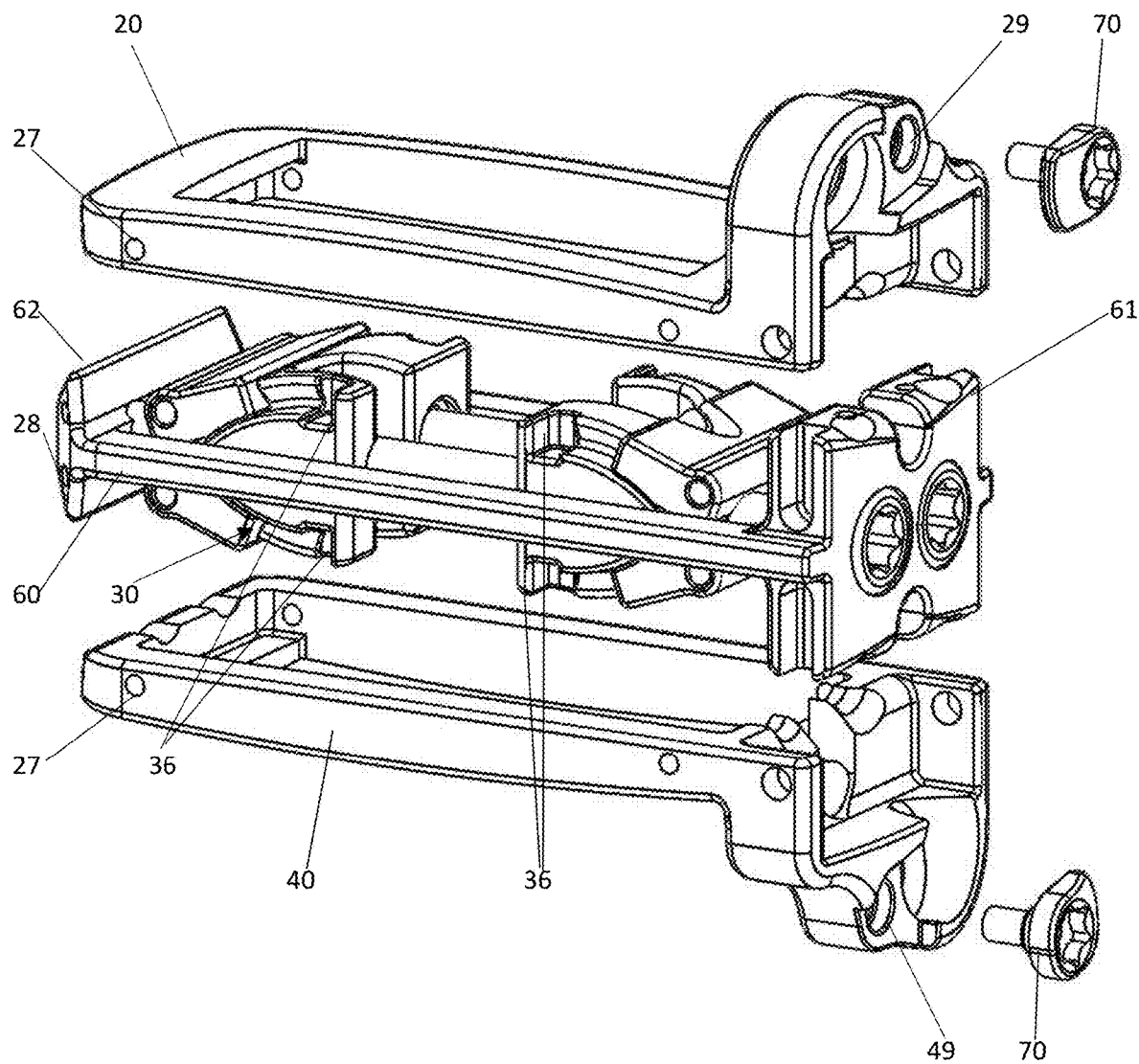
FIG. 6C is a perspective view of the assembled frame, ramp assemblies, drive shafts and pins of FIG. 6B with the base plates and locking tabs shown exploded as a third assembly step.
Figure 6D:
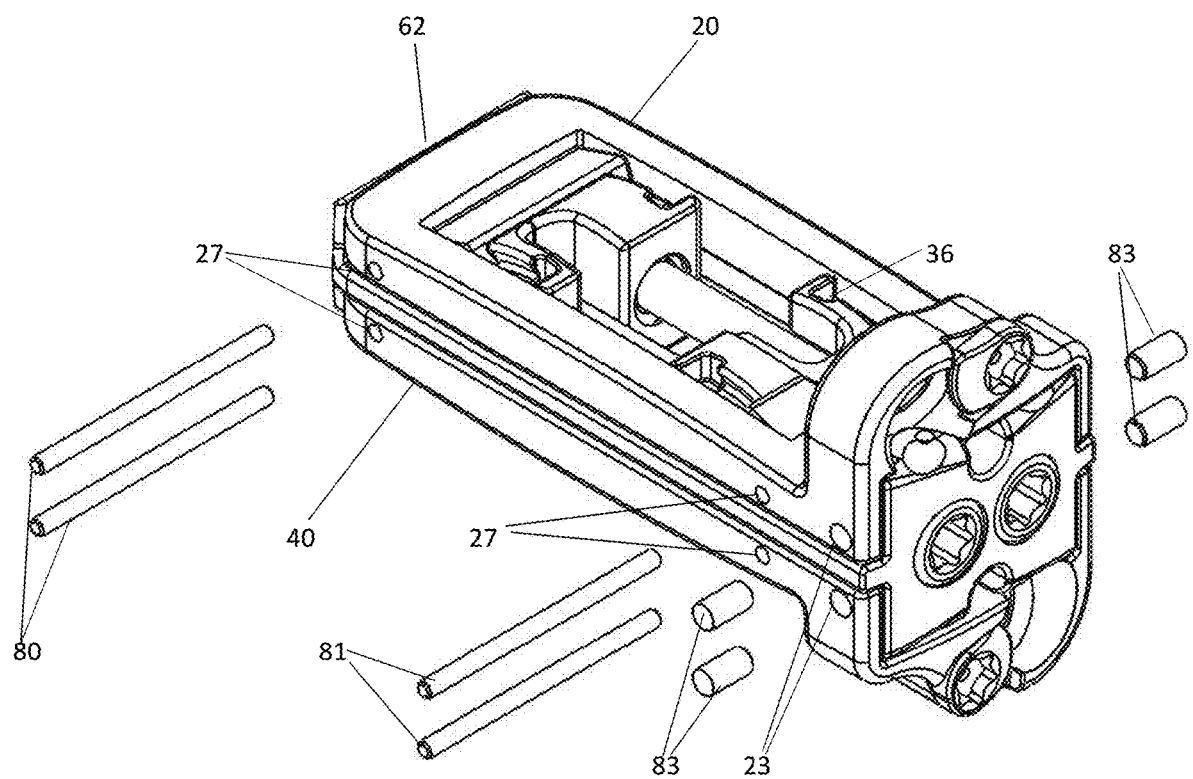
FIG. 6D is a perspective view of the assembled frame, ramp assemblies, drive shafts, pins, base plates and locking tabs of FIG. 6C with the final pins shown exploded as a fourth assembly step.

With reference to FIGS. 6A-6D, various exploded views of the components of the implant device 10 are shown. With reference to FIG. 6A, the ramp assemblies 30, 32 are shown as individual components, the translating ramps 34, 35 and the pivoting hinged ramps 31, 33 respectively are illustrated. As shown the translating ramps 34, 35 have an outer contour 37 on both an upper and a lower surface of each translating ramp 34, 35 and have a groove 38 on each ramp 34, 35. This groove 38 allows lateral sides of the pivoting hinged ramps 31 and 33 to enter in a dovetail configuration and lock into the translating ramps 34, 35. The inner surface 39 of both the pivoting hinged ramps 31, 33 ride on the outer surface 37 of the translating ramps 34 and 35 respectively. In this fashion, during the elevation of the implant 10 from contracted to expanded, the pivoting hinged ramps 31, 33 rest securely on the surface 37 on both lateral sides of the translating ramp 34, 35 such that the base plates 20, 40 hinged to the pivoting hinged ramps 31, 33 at both lateral ends are fully supported across the lateral width of the implant device 10. With reference to the frame 60, shown slightly below the ramp assembly components, the frame 60 is a singular piece having a distal end 62 that has a tapered exterior surface to facilitate insertion. With reference to the proximal end 61, grooves 63 are shown extending vertically, these grooves 63 are provided such that the end plates 21, 41 on the first base plate 20 and second base plate 40 can be pinned and slidably moved within the grooves 63 or slots on the end plates 21, 41 such that on expansion of the proximal end 61 the end plates 21, 41 can pivot about pins 83 inserted through the end plates 21, 41. This is best illustrated in FIGS. 6C and 6D. The pins 83, as shown in FIG. 6D, engage the end plates 21, 41 and are pressed into holes 23 provided in each end plate 21, 41. These holes 23 and pins 83 are shown such that the pins 83 extend sufficiently inwardly to be captured within the slot or groove 63 in the proximal end 61. As further shown in FIG. 6B, are a pair of drive shaft pins 82, these drive shaft pins 82 extend through the holes 28 in the distal end of the frame 60. These holes 28 extend across the frame 60 in such a fashion that the distal pins 82 will engage grooves 53, shown in FIG. 6B, at the distal end of the drive shafts 50, 52. At the proximal end 61, pins 85 are pushed through holes in the end plate 64 and will lock into grooves 55 at the proximal end of the drive shafts 50, 52. These pins allow the drive shafts to be captured within the frame 60 while allowing the drive shafts 50, 52 to be freely rotatably when positioned securely and affixed to the frame 60 by the use of these pins. With reference to FIG. 6C, the ramp assemblies 30, 32 and drive shafts 50, 52 are shown affixed to the frame 60 with the first base plate 20 and second base plate 40 shown above that assembly. A locking means or tab 70 is illustrated that is affixed into an opening 29 and 49 in the two opposing end plates 21 and 41, respectively. These locking tabs 70, when rotated over the head of the fastener 100, prevent the fastener 100 from backing out. This effectively completes the assembly of the implant device 10. As further shown in FIG. 6D, the pivoting hinged ramps 31, 33 are pinned to the base plates 20, 40 through holes 27 in the base plates and holes 22 in the pivoting hinged ramps with pins 80, 81.

Figure 7A:
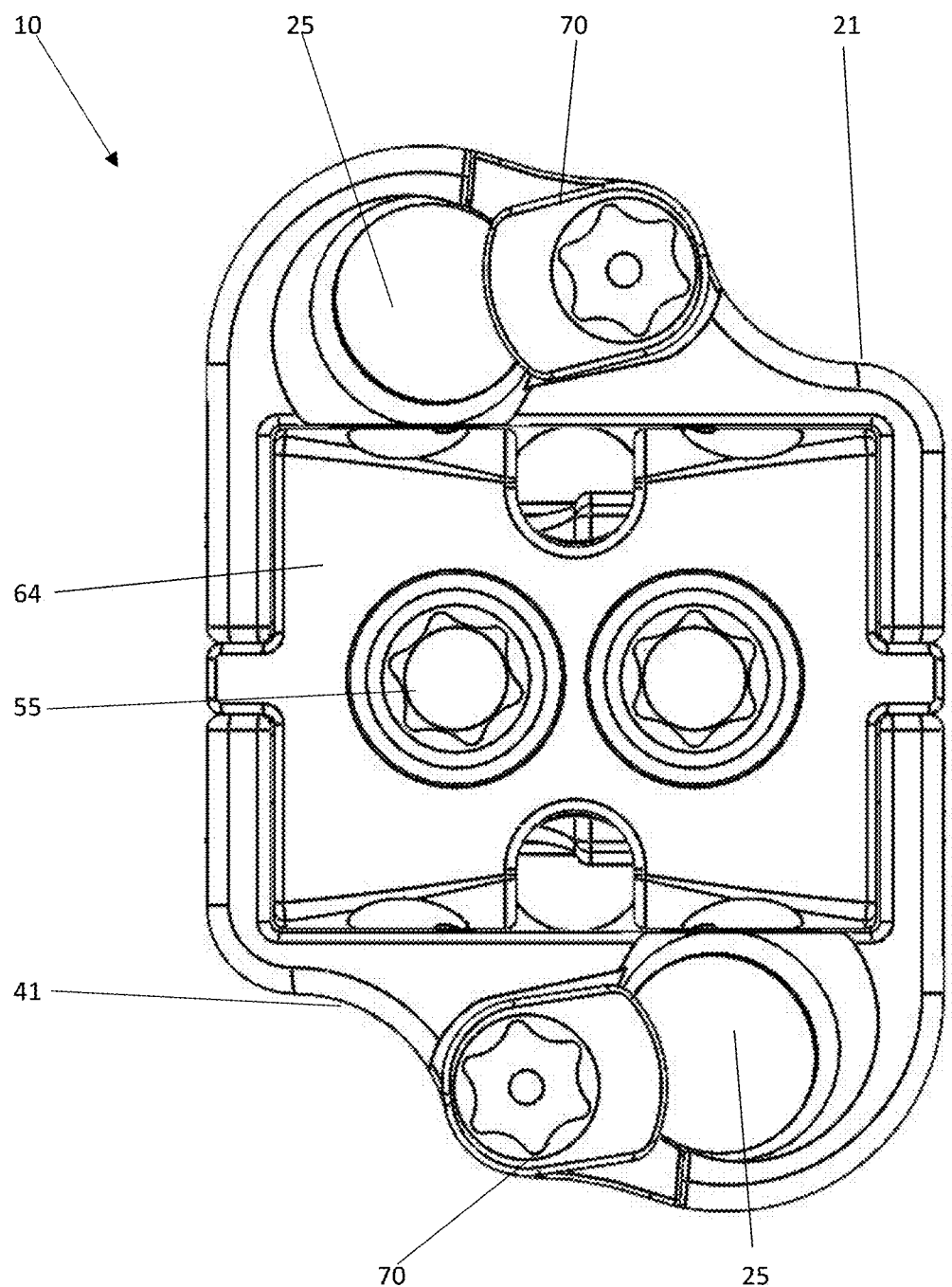
FIG. 7A is a front or proximal view of the device of the present invention shown in a contracted position.
Figure 7B:
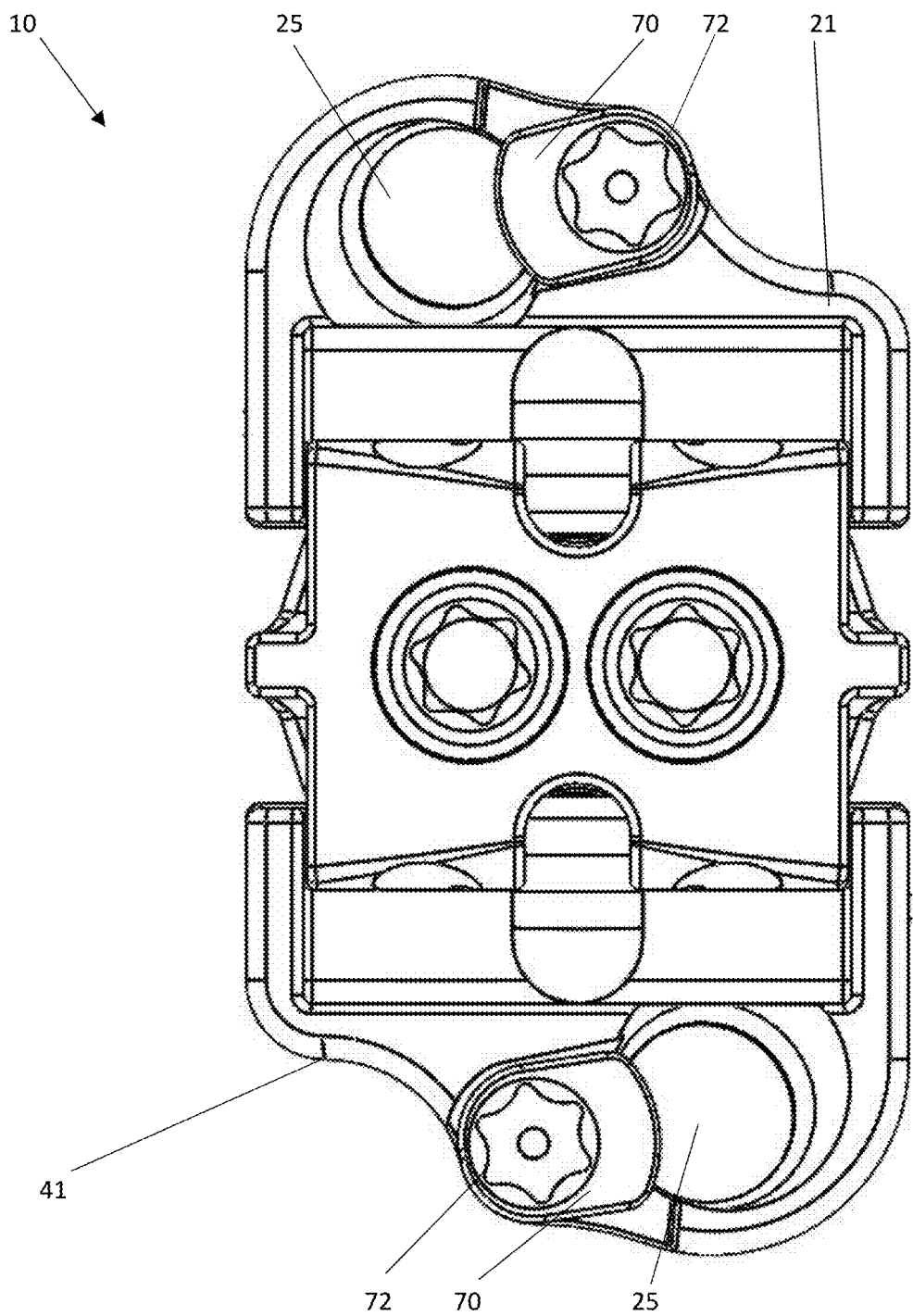
FIG. 7B is a front or proximal view of the device of the present invention shown in an expanded position.
Figure 7C:
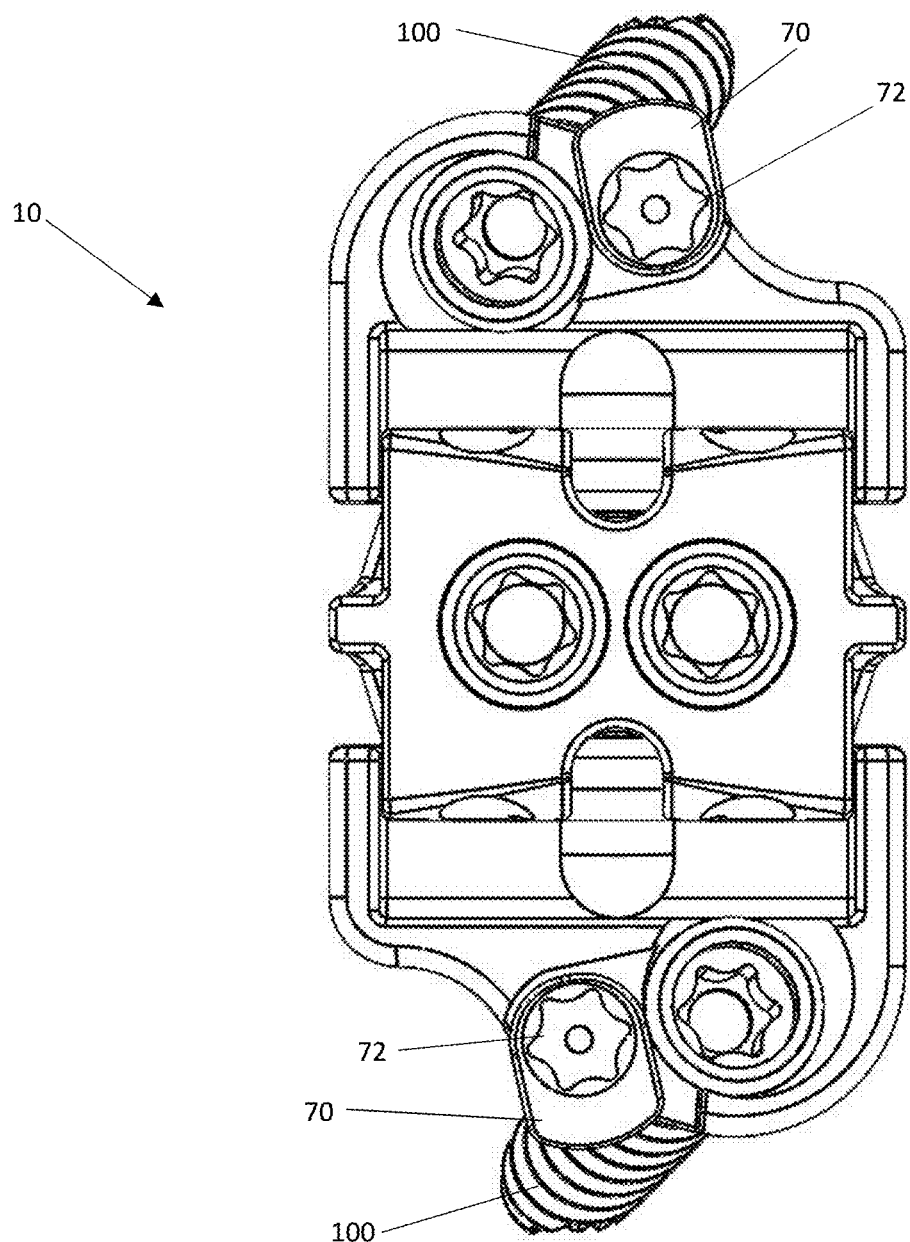
FIG. 7C is a front or proximal view of the device of the present invention shown in an expanded position with threaded fasteners installed in the proximal end of each first and second base plate and the locking tabs in an unlocked position.
Figure 7D:
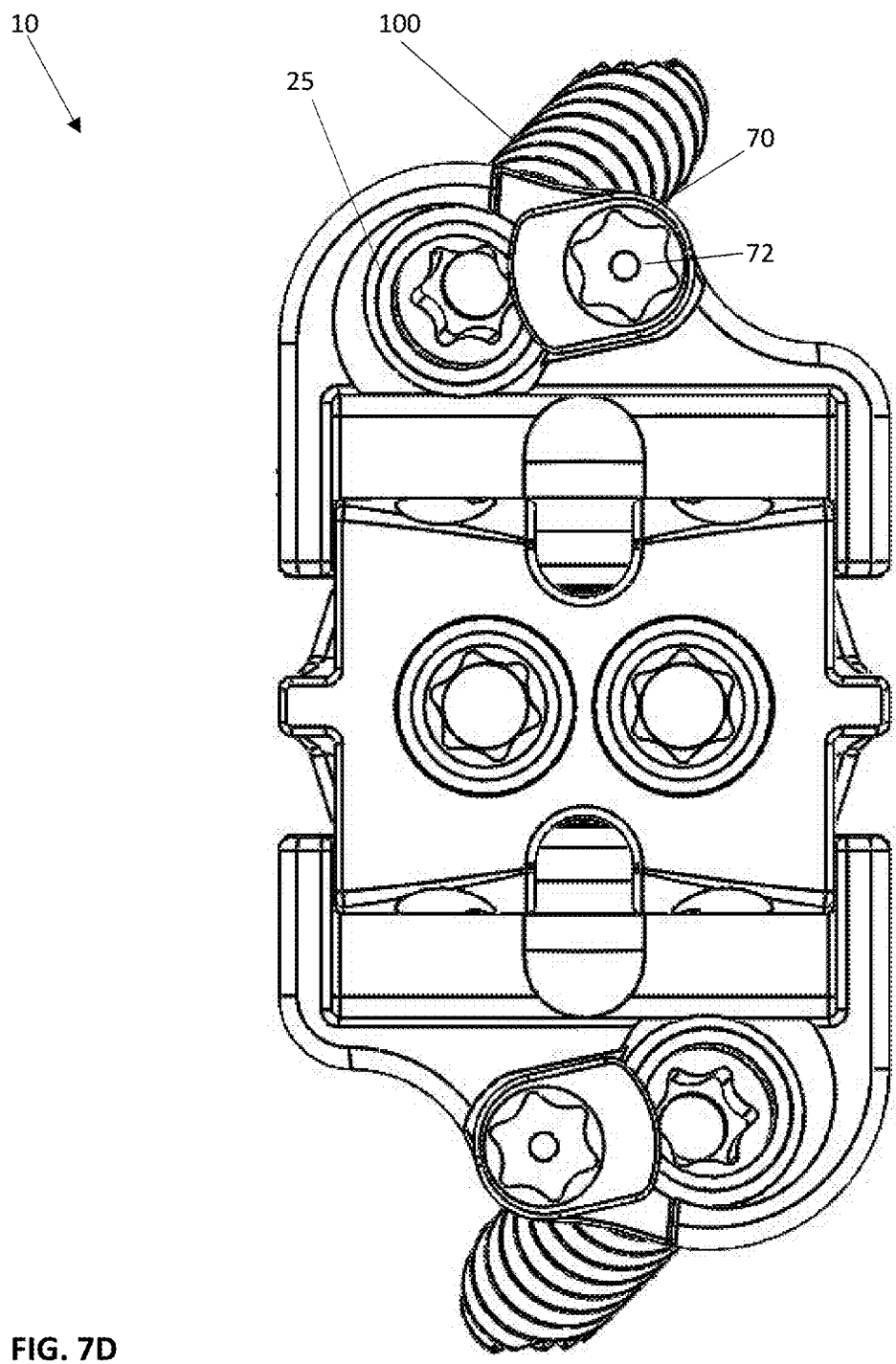
FIG. 7D is a front or proximal view of the device of the present invention shown in an expanded position with threaded fasteners installed in the proximal end of each first and second base plate and the locking tabs in a locked position.

With reference to FIGS. 7A-7D, end views of the implant device 10 are illustrated. With reference to FIG. 7A, the implant device 10 is shown in the fully contracted position. The implant device 10, at the proximal end 61, shows the fastener openings 25 with the locking tab 70 projecting over a portion of the fastener opening hole 25. In this condition, the fasteners 100 have yet to be inserted into place and could not be until the locking tab 70 is moved into an open position. With reference to FIG. 7B, the implant device 10 is shown in a fully expanded position as compared to FIG. 7A wherein the implant 10 was shown in the contracted position. With reference to FIG. 7C, when the implant device 10 is in the expanded position and inserted between the vertebral bodies, not shown, the fasteners 100 can be inserted through the openings 25 wherein they can be delivered to and fastened to the two vertebral bodies. To accomplish this, the locking tab 70 is rotated with a drive tool, not shown, and the star shaped recess 72 so the opening 25 is fully exposed to allow the head of the fastener 100 to be inserted into the hole opening 25 on insertion. With reference to FIG. 7D, the locking tab 70 is then shown in the locked position, rotated and covering at least partially the hole opening 25, thereby preventing the fastener 100 from loosening and backing out once inserted and threaded into the vertebral body.

Figure 8A:
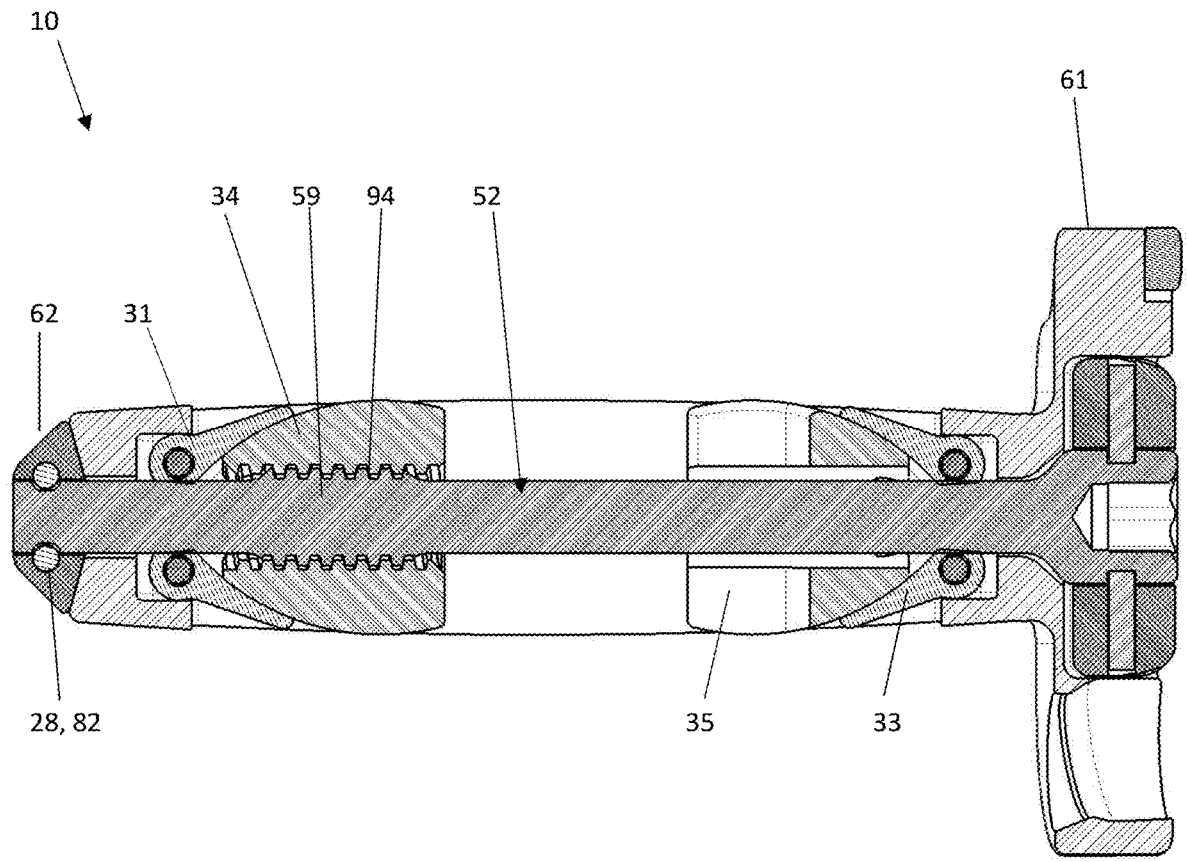
FIG. 8A is a side cross-sectional view of the device of the present invention with the distal drive shaft collapsed.
Figure 8B:
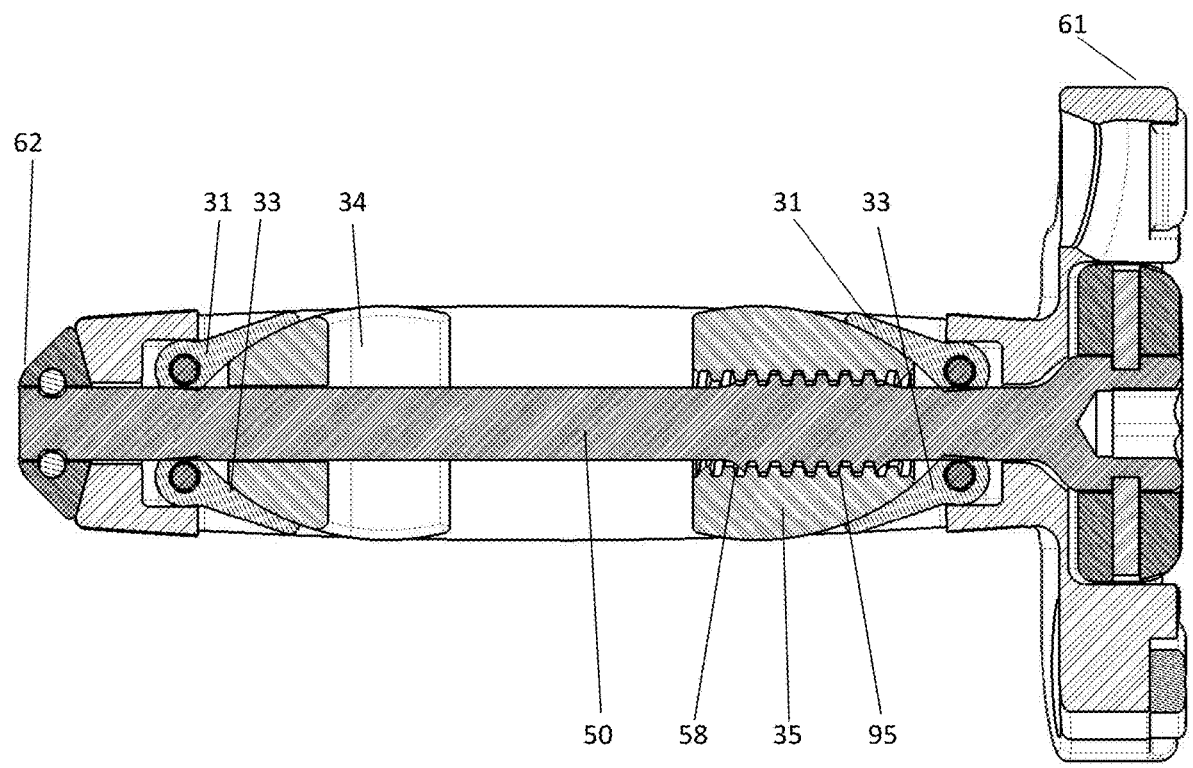
FIG. 8B is a side cross-sectional view of the device of the present invention with the proximal drive shaft collapsed.
Figure 8C:
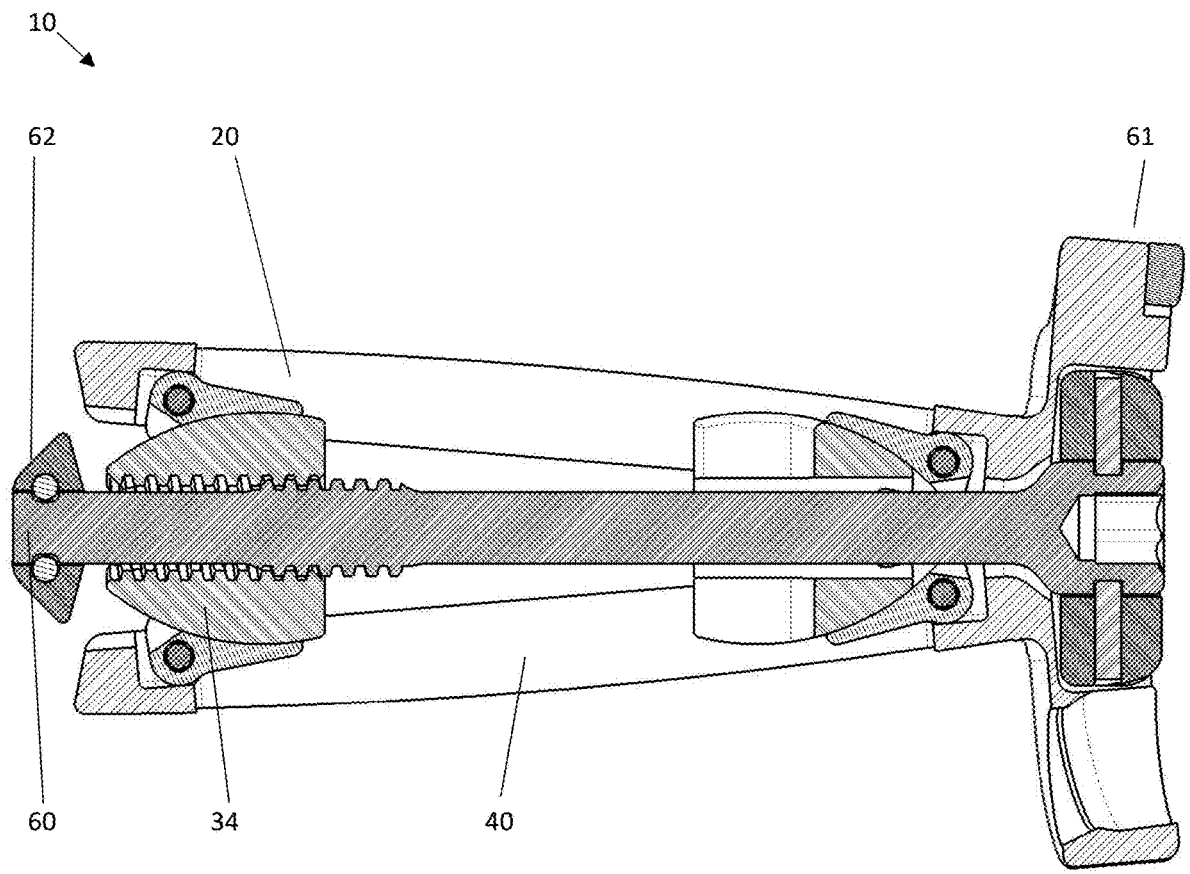
FIG. 8C is a side cross-sectional view of the device of the present invention with the distal drive shaft distally expanded.
Figure 8D:
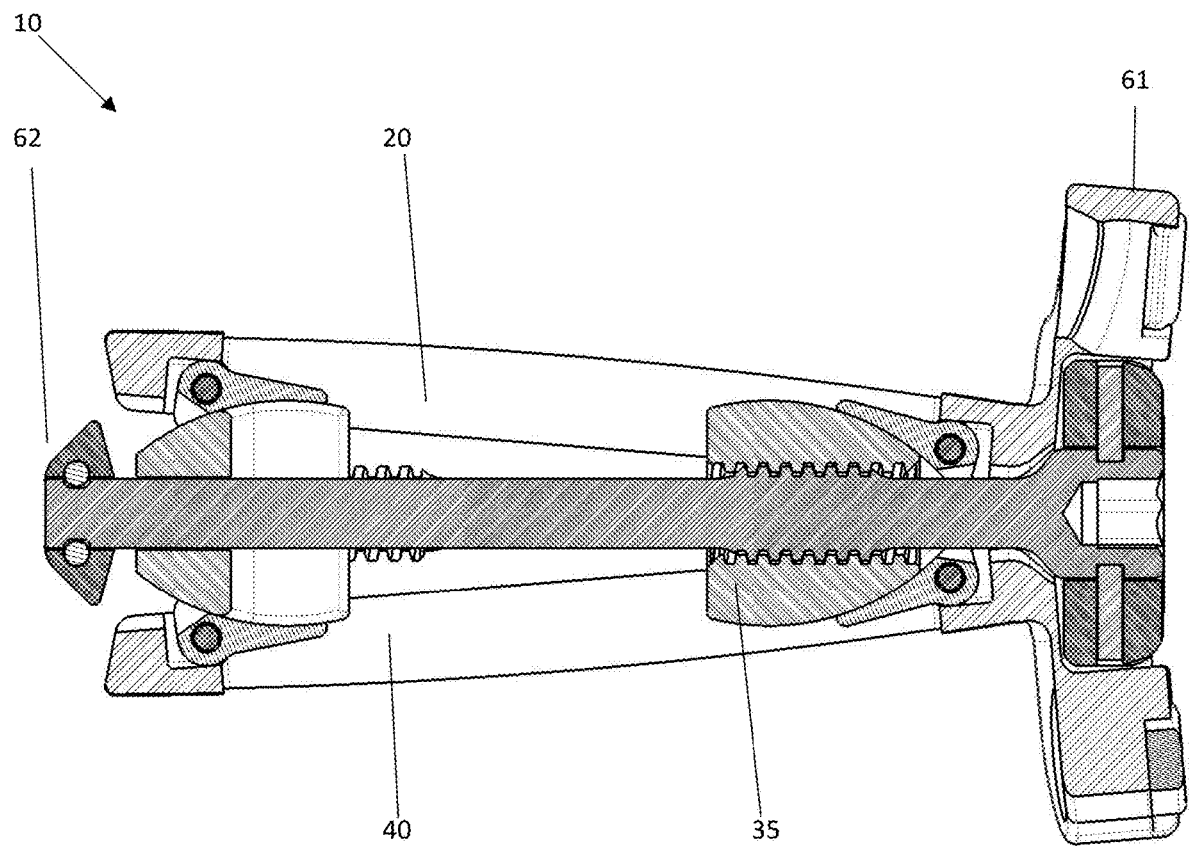
FIG. 8D is a side cross-sectional view of the device of the present invention with the proximal drive shaft distally expanded.
Figure 8E:
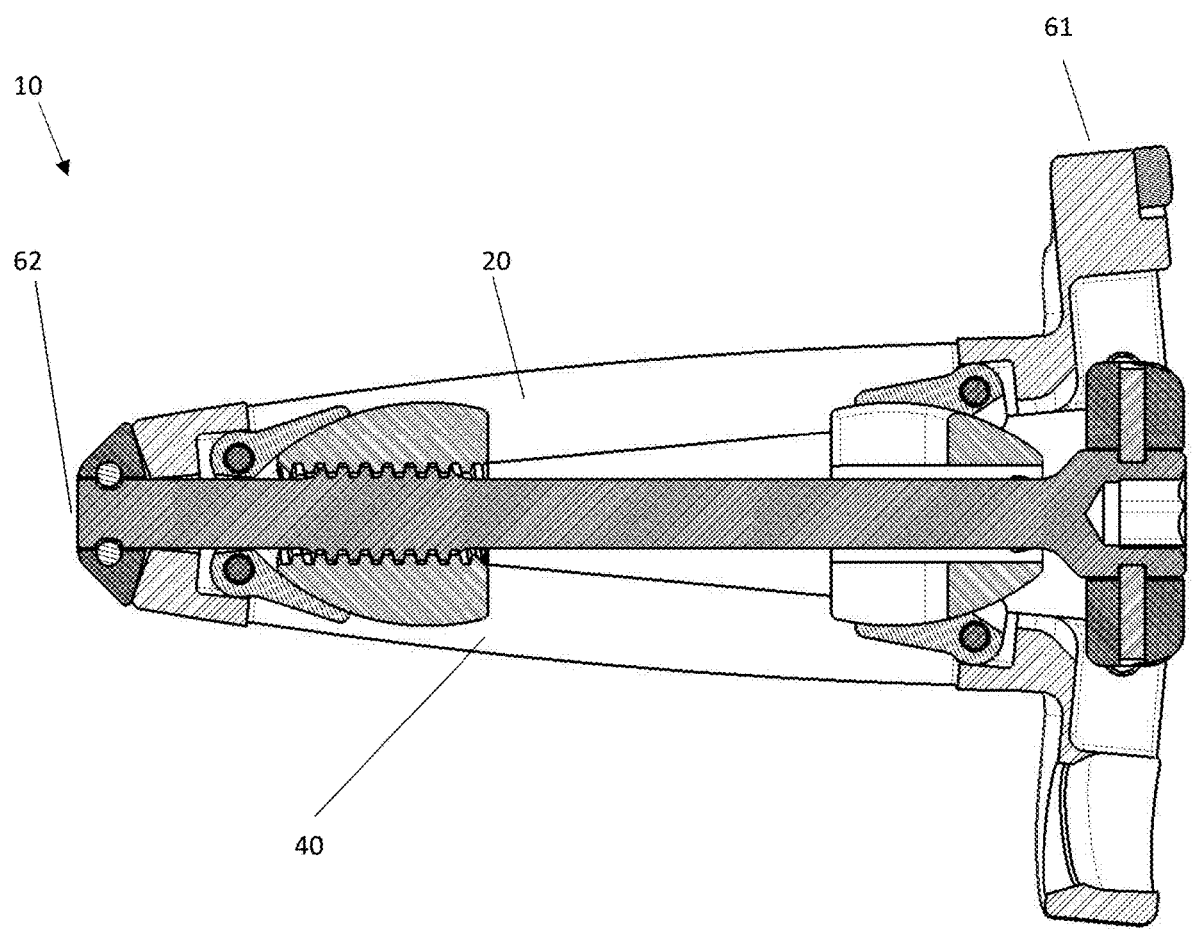
FIG. 8E is a side cross-sectional view of the device of the present invention with the distal drive shaft proximally expanded.
Figure 8F:
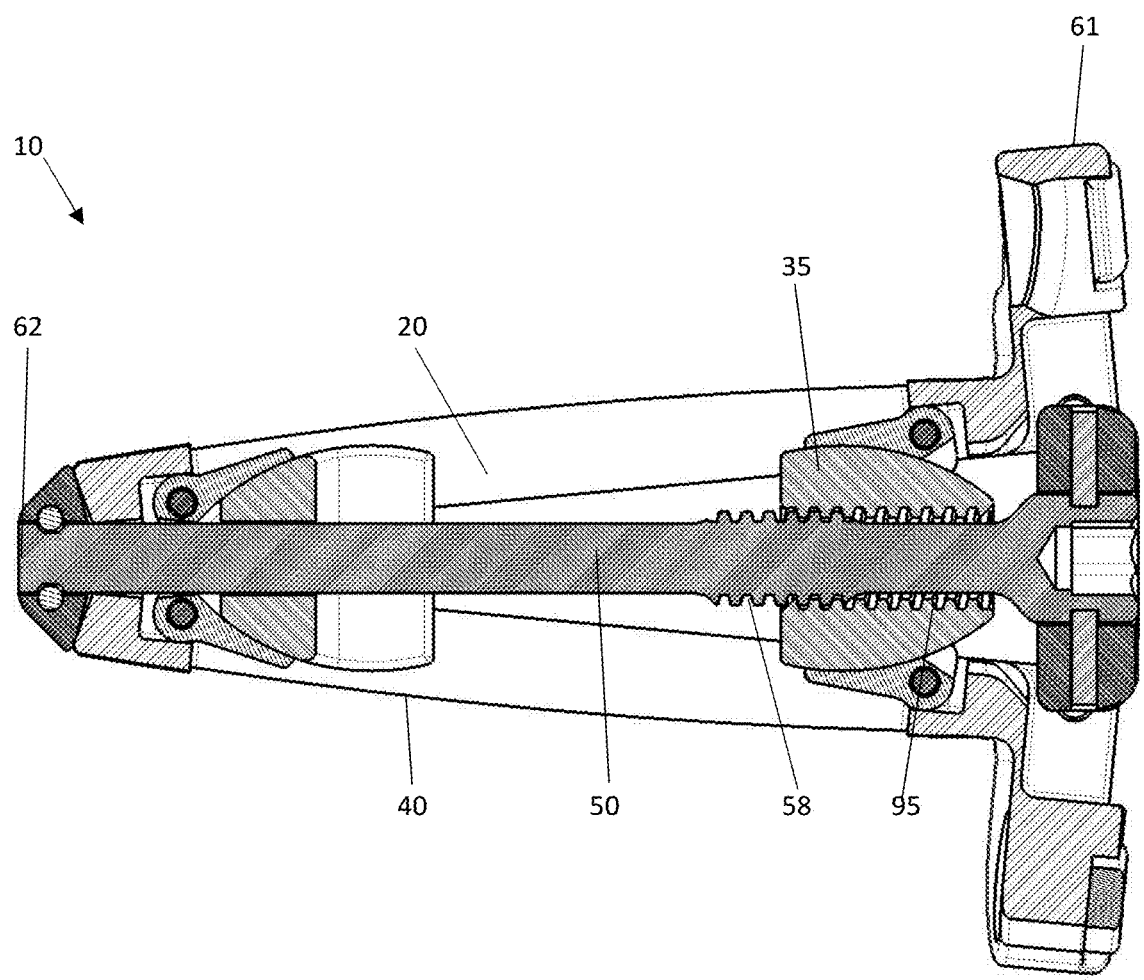
FIG. 8F is a side cross-sectional view of the device of the present invention with the proximal drive shaft proximally expanded.
Figure 8G:
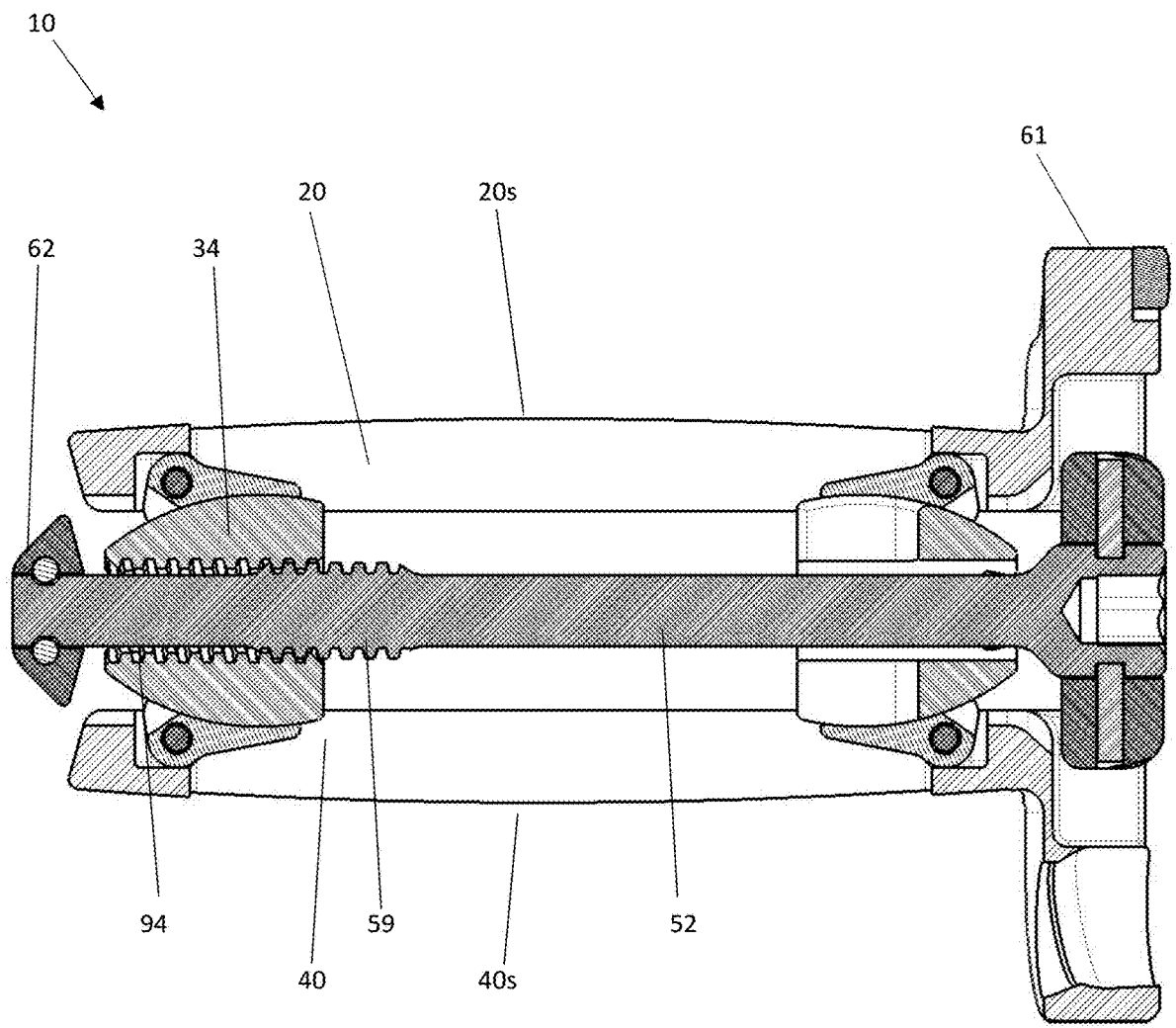
FIG. 8G is a side cross-sectional view of the device of the present invention with the distal drive shaft fully expanded.
Figure 8H:
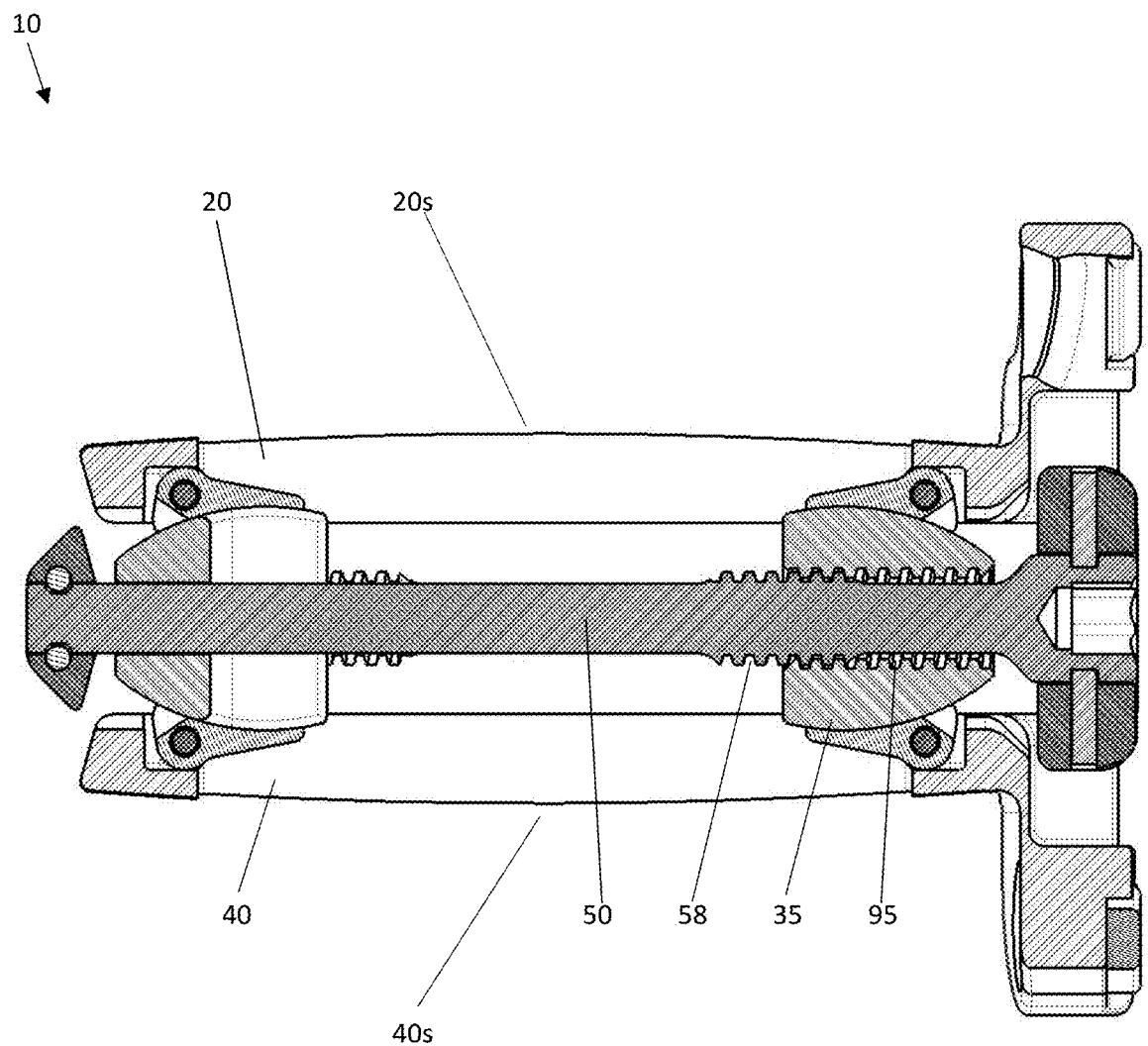
FIG. 8H is a side cross-sectional view of the device of the present invention with the proximal drive shaft fully expanded.

With reference to FIGS. 8A-8H, various cross-sectional views of the implant device 10 are illustrated. These cross-sectional views are taken down the longitudinal length of the device 10 in such a way that either the proximal drive shaft 50 or the distal drive shaft 52 is shown, the cross section taken through the middle of the respective drive shaft 50, 52. As shown in FIG. 8A, the distal drive shaft 52 is shown with the implant device 10 in the fully contracted position. In this case, the pivoting hinged ramps 31, 33 are shown at the lowest height on the contoured surfaces 37 of the translating ramps 34, 35 of ramp assembly 30, 32 respectively. As can be seen, the pivoting hinged ramps 31, 33 ride on the exterior surface 37 of the translating ramps 34, 35 and in the contracted position are fully contained and pinned to the respective base plates, 20, 40. As further shown, the pins 82 holding the distal end of the drive shafts 50, 52 are shown holding the drive shafts in place at the distal end 62, similarly the pins 85 shown extending through the end plate 64 of the frame 60 are shown holding the drive shafts 50, 52 at the proximal end 61. There is a drive opening 55, shown as a star shaped recess, provided at the proximal end such that the rotation of each drive shaft 50, 52 can be accomplished by the insertion of a drive tool, not illustrated. With reference to the drive shaft 52, threads 59 are shown in engagement with complimentary female threads 94 on the translating ramp 34 to be moved. As shown in the contracted position, these threads 94 are fully inside the translating ramp 34. With reference to FIG. 8B, the proximal drive shaft 50 is illustrated having the threads 58 fully engaged in the threads 95 of the proximal ramp 35, again, this is in the fully contracted position, as previously discussed in reference to FIG. 8A. With reference to FIG. 8C, when the implant 10 is expanded at the distal end 62, the translating ramp 34 is moved progressively towards the distal end 62 of the frame 60 and as it moves toward the end of the frame 60, the pivoting hinged ramps 31, 33 slide up the contour on the exterior surface 37 of the translating ramp 34 elevating the base plates 20, 40 respectively. As shown, the translating ramps 34, 35 are equally contoured, therefore, when the drive shaft 52 is rotated and the threads 59 drive the translating ramp 34 toward the distal end 62, the base plates 20, 40 move equally expanding away from the fully contracted position. With reference to FIG. 8D, when this occurs, the proximal drive shaft 50 has not been moved where the threads 58 are still inside the proximal translating ramp 35 engaging the threads 95. With reference to FIGS. 8E and 8F, the implant 10 is shown with the proximal end 61 expanded and the distal end 62 contracted. When the proximal end 61 of the implant 10 is expanded, the distal translating ramp 34 is shown in the contracted position with the threads 59 from the distal drive 52 shaft still fully engaged in threads 94 inside the translating ramp 34. Correspondingly, when the proximal drive shaft 50 is rotated, it drives the proximal translating ramp 35 towards the proximal end 61 of the implant 10 as the threads push it toward the proximal end of the implant 10 elevating the base plates 20, 40 and as previously discussed, since the ramps 34, 35 are symmetrical in this configuration both base plates 20, 40 move equally apart at the proximal end 61. Interestingly, when this occurs, you will notice that the end plates 21, 41 being integral to the base plates 20, 40 will elevate accordingly, as this occurs, they slide and rotate on the same inclination as the base plates. With reference to FIGS. 8G and 8H, when both translating ramps 34, 35 are moved into the fully expanded position, the base plates 20, 40 are relatively horizontal and parallel to each other, with the caveat that there is a slight contour 20s, 40s on the outer surface of each base plate 20, 40 as previously discussed. This contour is quite beneficial as it provides the ability of the implant device 10 to provide a solid mimicking of the endplates of the vertebral bodies that will be supported on implantation. When these convex contours 20s, 40s are positioned within the vertebral body 2, 4, a slight inclination of the base plates 20, 40 still affords a wide surface area of support at the implant 10 as opposed to wedge type devices with straight inclinations on their outer surface. As an alternative embodiment, the outer surface of the base plates 20, 40 have an angle mimicking the lordotic curvature of the lumbar spine at multiple angles, as will be discussed with reference to FIGS. 17A-19B. As shown in FIG. 8G, the distal ramp assembly 30 is fully moved toward the expanded position when the distal translating ramp 34 is moved toward the distal end 62 of the implant 10. Similarly, the proximal ramp assembly 35 is moved toward the proximal end 61 of the implant 10. Since they are both moved, the pivoting hinged ramps 31, 33 are elevated by riding on the contoured surface 37 of the translating ramps 34, 35 increasing the height of the implant device 10 to the fully expanded position as shown in FIG. 8H.

Figure 9A:
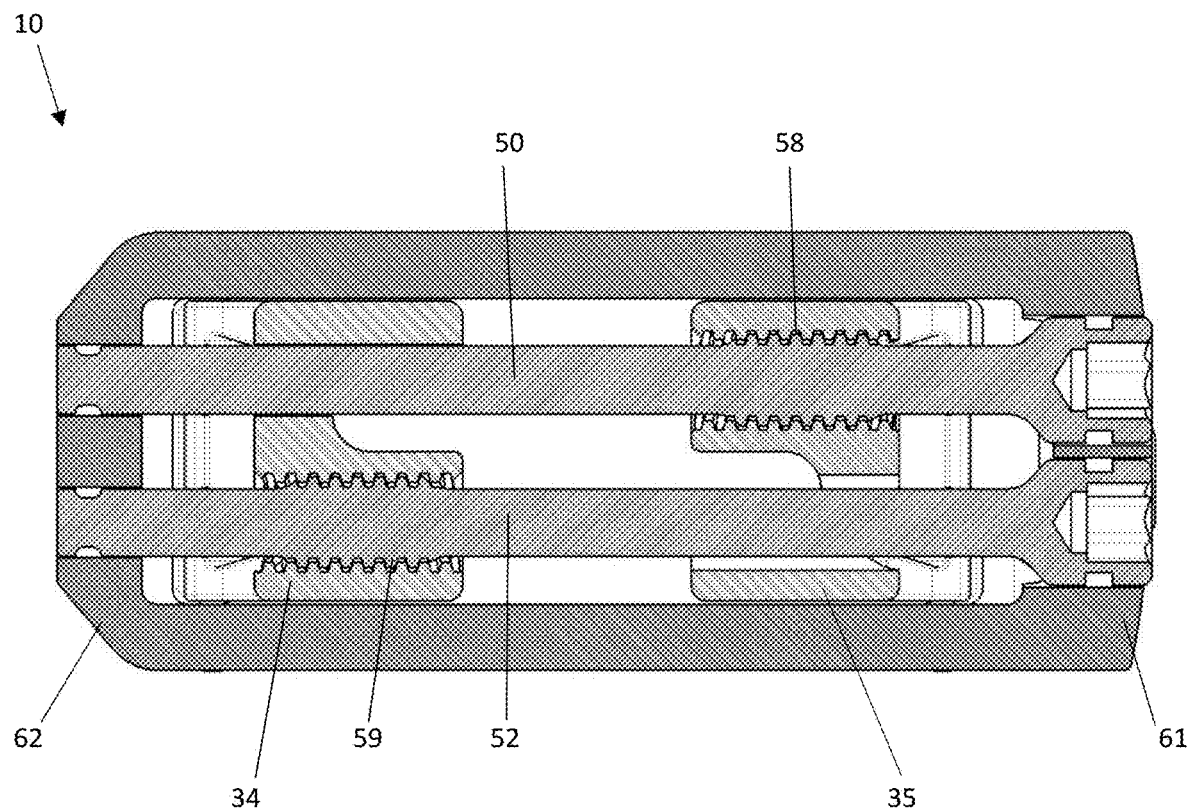
FIG. 9A is a top cross-sectional view of the device of the present invention in a contracted position.
Figure 9B:
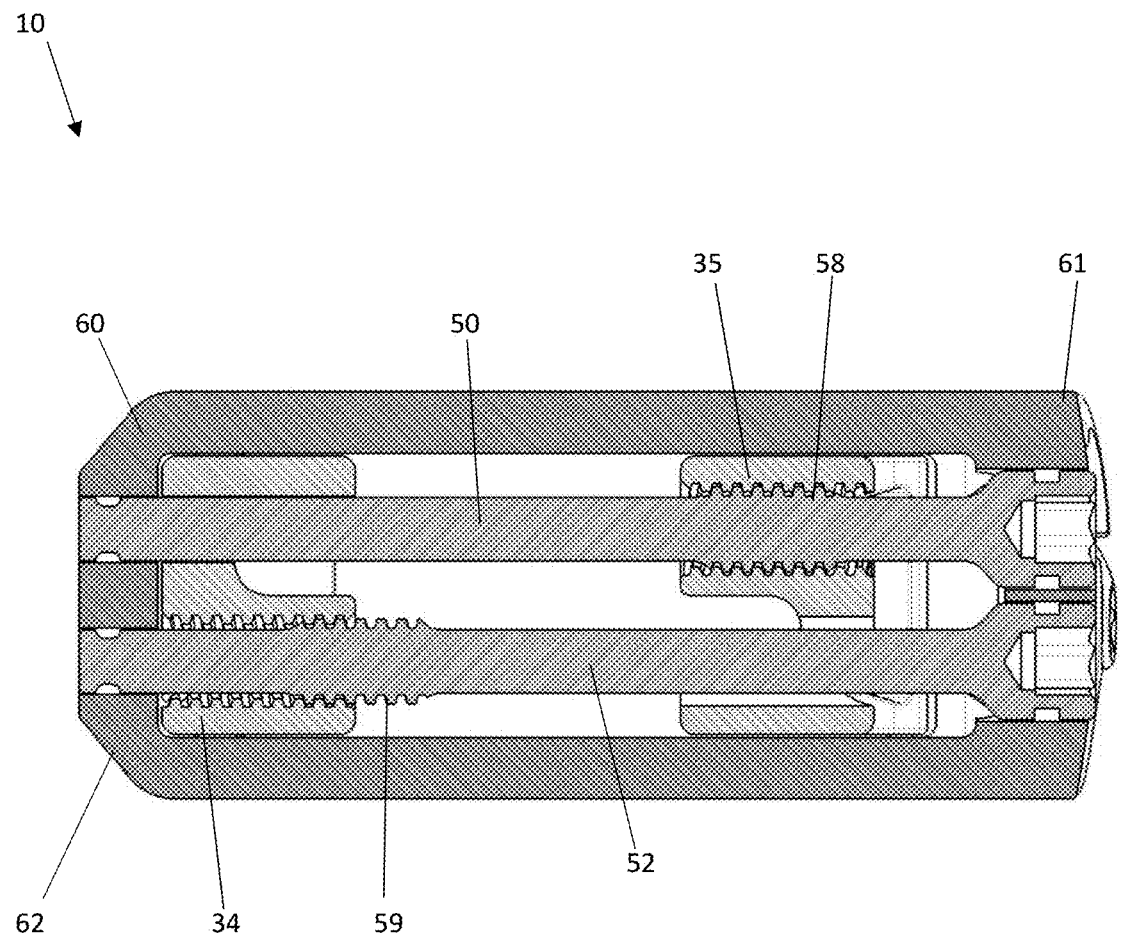
FIG. 9B is a top cross-sectional view of the device of the present invention in a distally expanded position.
Figure 9C:
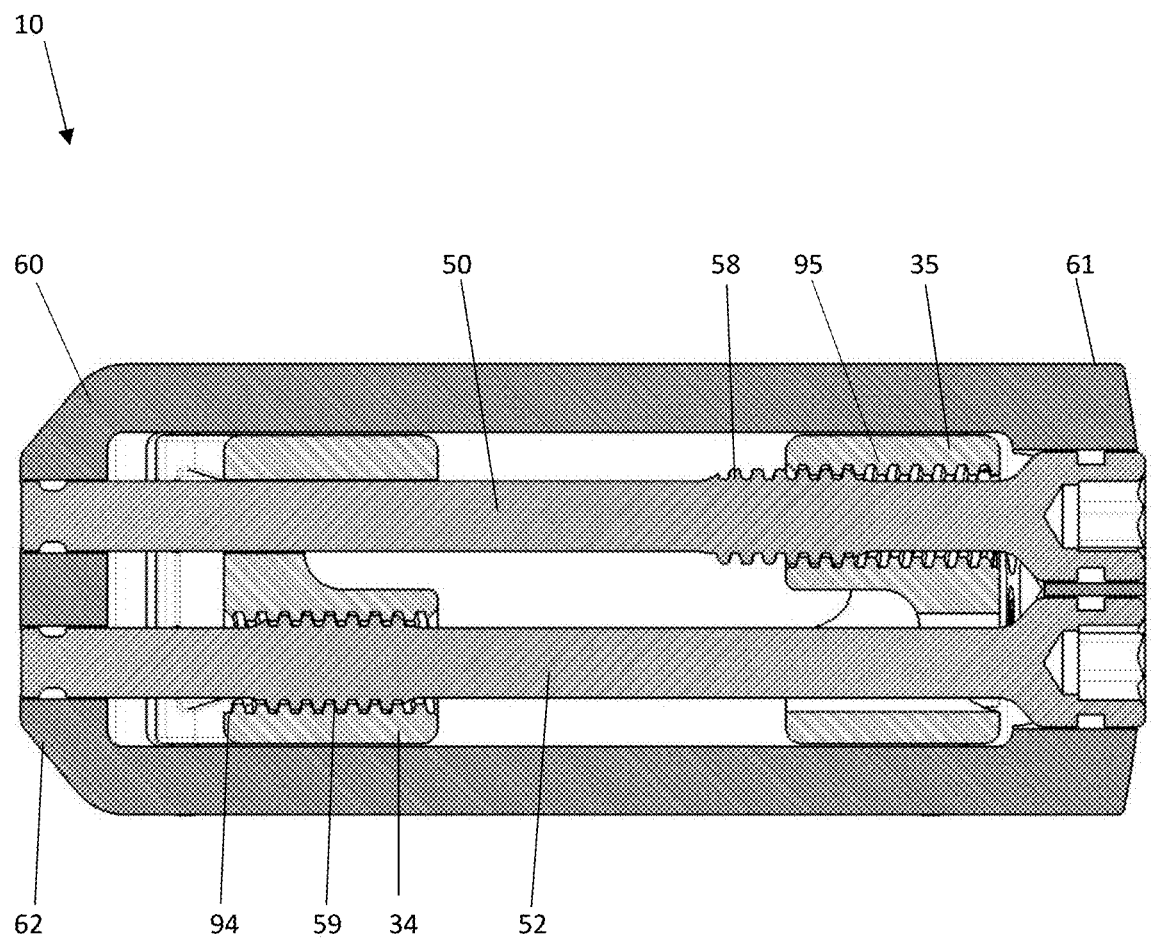
FIG. 9C is a top cross-sectional view of the device of the present invention in a proximally expanded position.
Figure 9D:
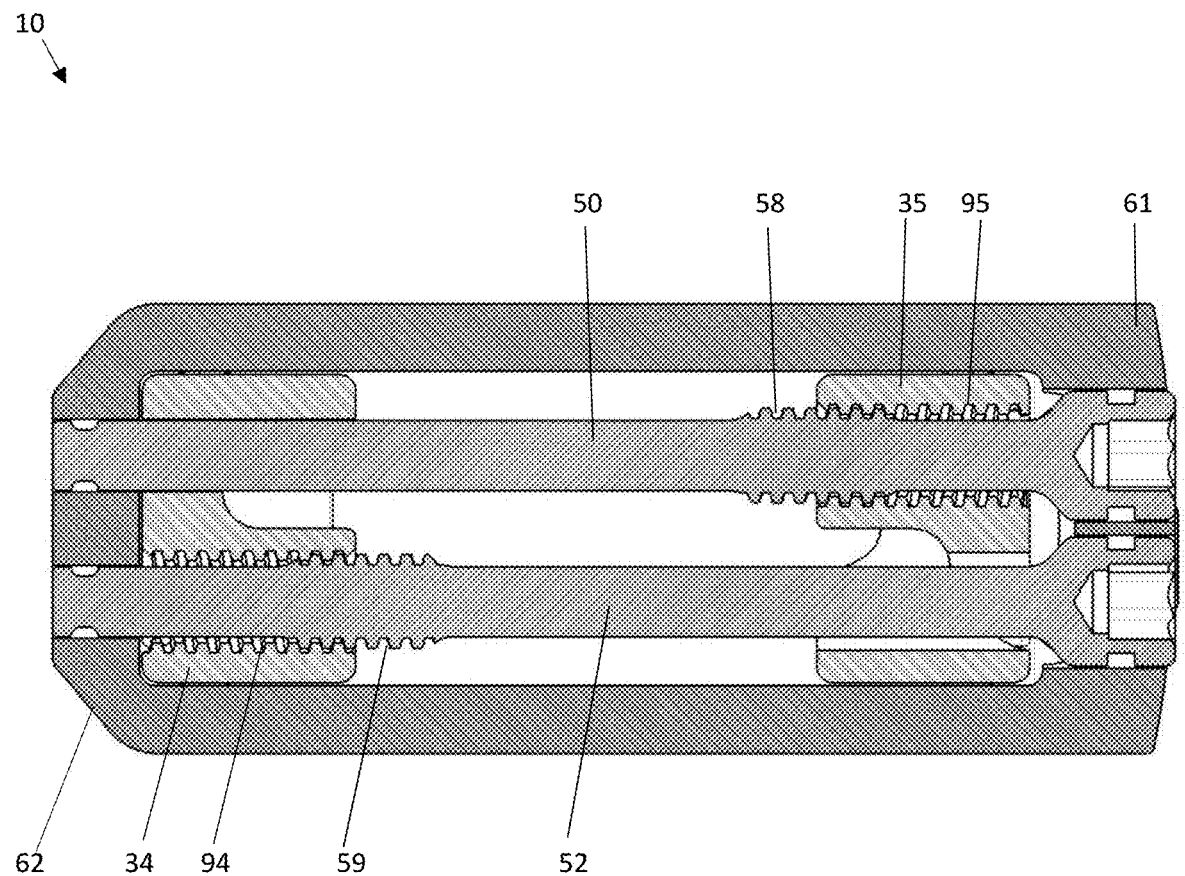
FIG. 9D is a top cross-sectional view of the device of the present invention in a fully expanded position.

With reference to FIG. 9A-9D, top cross sectional views are shown to facilitate an understanding of the ramp assemblies 30, 32. With reference to FIG. 9A, the translating ramps 34, 35 are shown in the contracted position, thus are spaced away from the distal 62 and proximal 61 ends, as illustrated. In such a configuration, the threads 58, 59 on each drive shaft 50, 52 are fully encased within their respective translating ramps 34, 35. With reference to FIG. 9B, when the distal end 62 is elevated from the contracted position as shown in FIG. 9A, the drive shaft 52 is shown with the threads 59 partially exposed wherein the translating ramp 34 at the distal end 62 is moved distally, almost into contact with the frame 60 at the distal end 62. With reference to FIG. 9C, shows the alternate configuration where the translating ramp 35 is moved toward the proximal end 61 of the implant 10 and the distal translating ramp 34 is shown in the contracted position. With reference to FIG. 9D, in the fully expanded configuration, both translating ramps 34, 35 are shown moved toward the distal 62 and proximal 61 ends and not spaced therefrom.

Figure 10A:
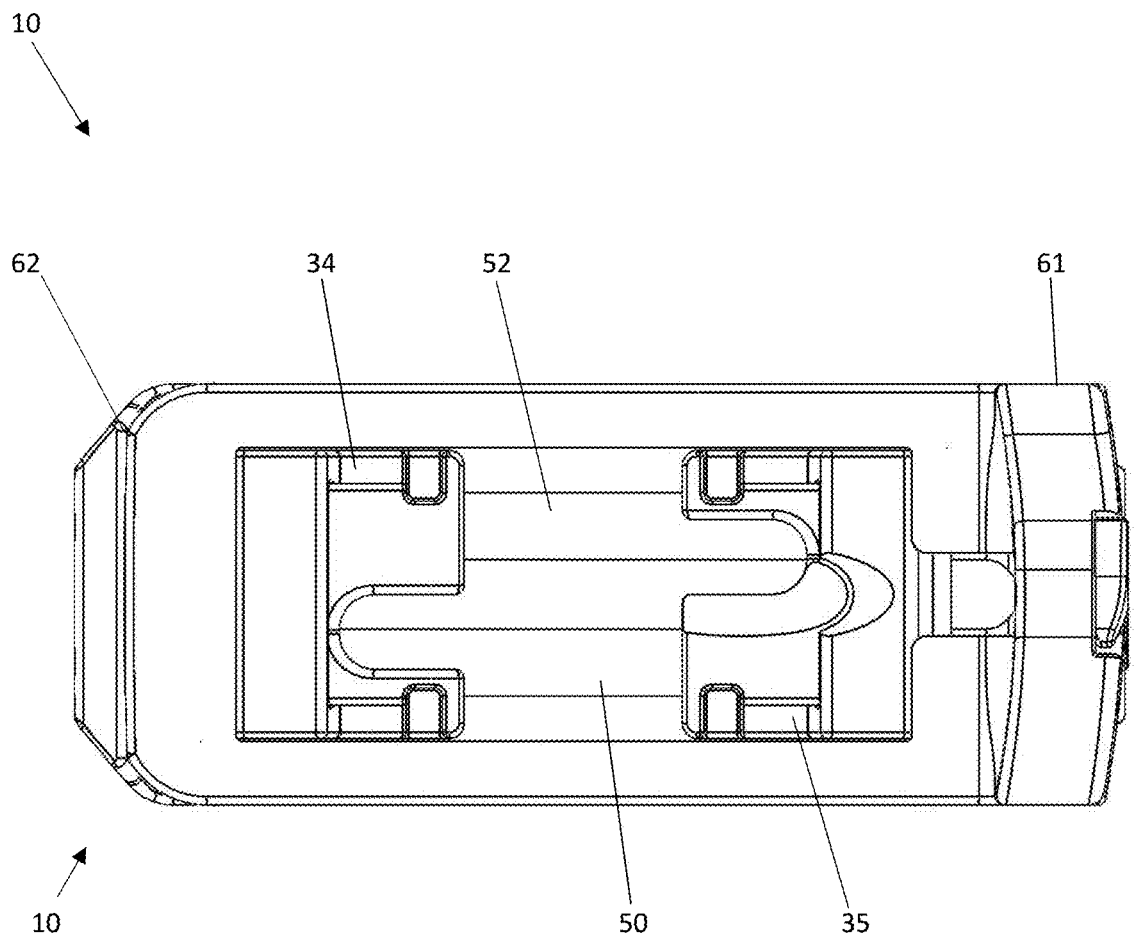
FIG. 10A is a top view of the device of the present invention in a contracted position.
Figure 10B:
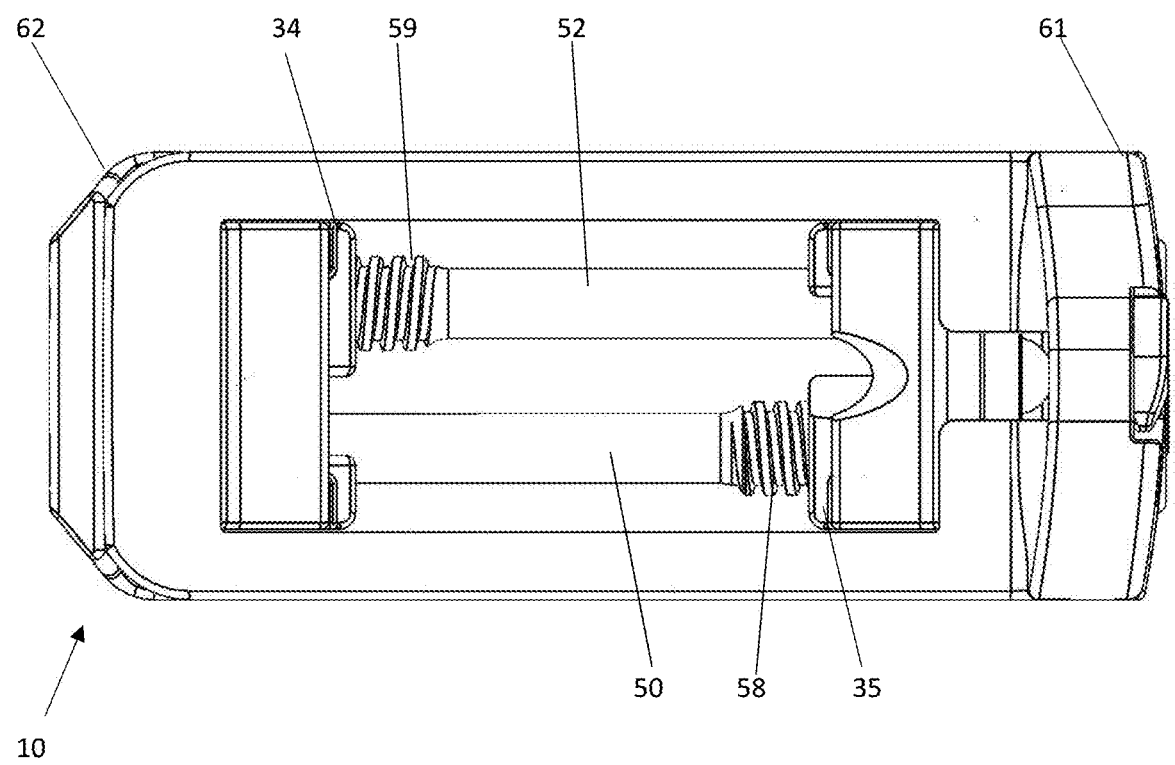
FIG. 10B is a top view of the device of the present invention in a fully expanded position.
Figure 10C:
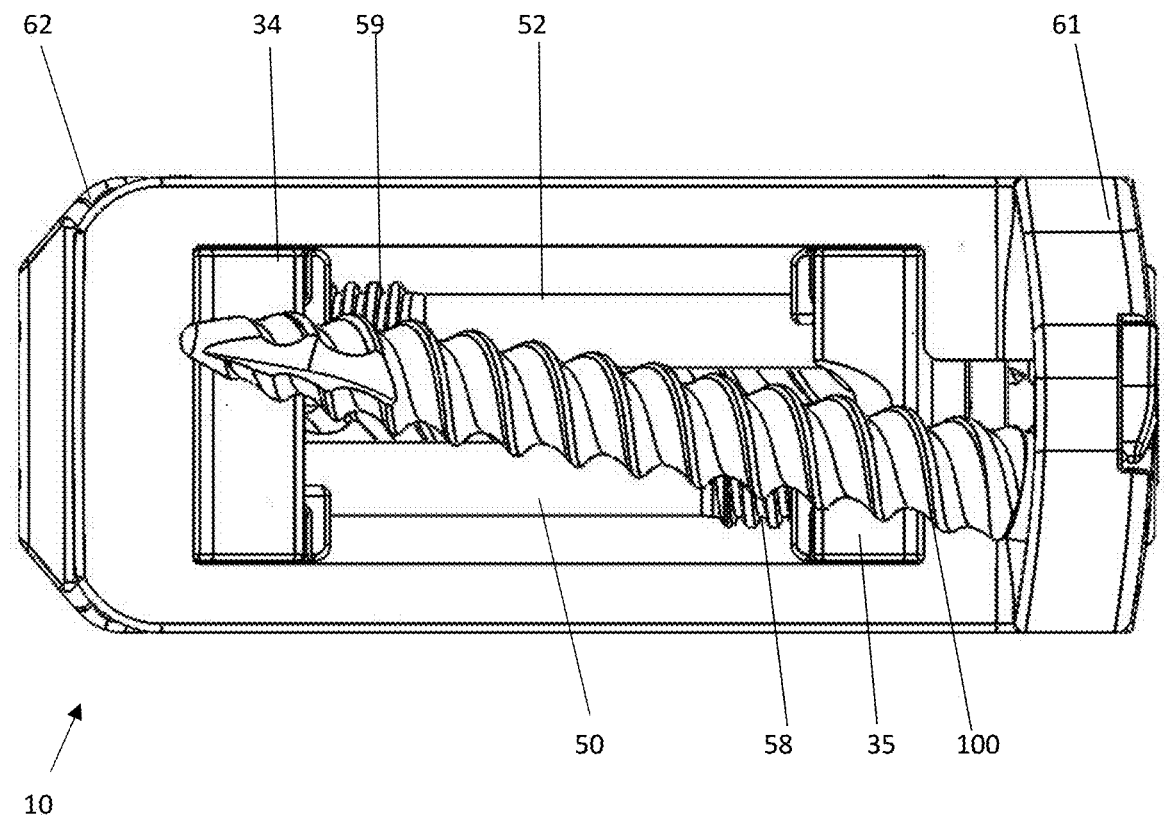
FIG. 10C is a top view of the device of the present invention in a fully expanded position with threaded fasteners installed in the proximal end of each first and second base plate.

With reference to FIGS. 10A-10C, an outline drawing of the implant device 10 from a top view is shown. In FIG. 10A, the device 10 is in a fully contracted position, whereas the top view of FIG. 10B shows the device in a fully expanded position. With reference to FIG. 10C, the implant device 10 is shown with threaded fasteners 100 inserted in the hole openings 25. It is hoped that these additional views showing how the device 10 is actually positioned during the various stages of inclination and various conditions from contracted to fully expanded and the ability of the device 10 to be distally expanded independent of proximal expansion and proximally expanded independent of distal expansion has been shown throughout the various views previously discussed.

Figure 11A:
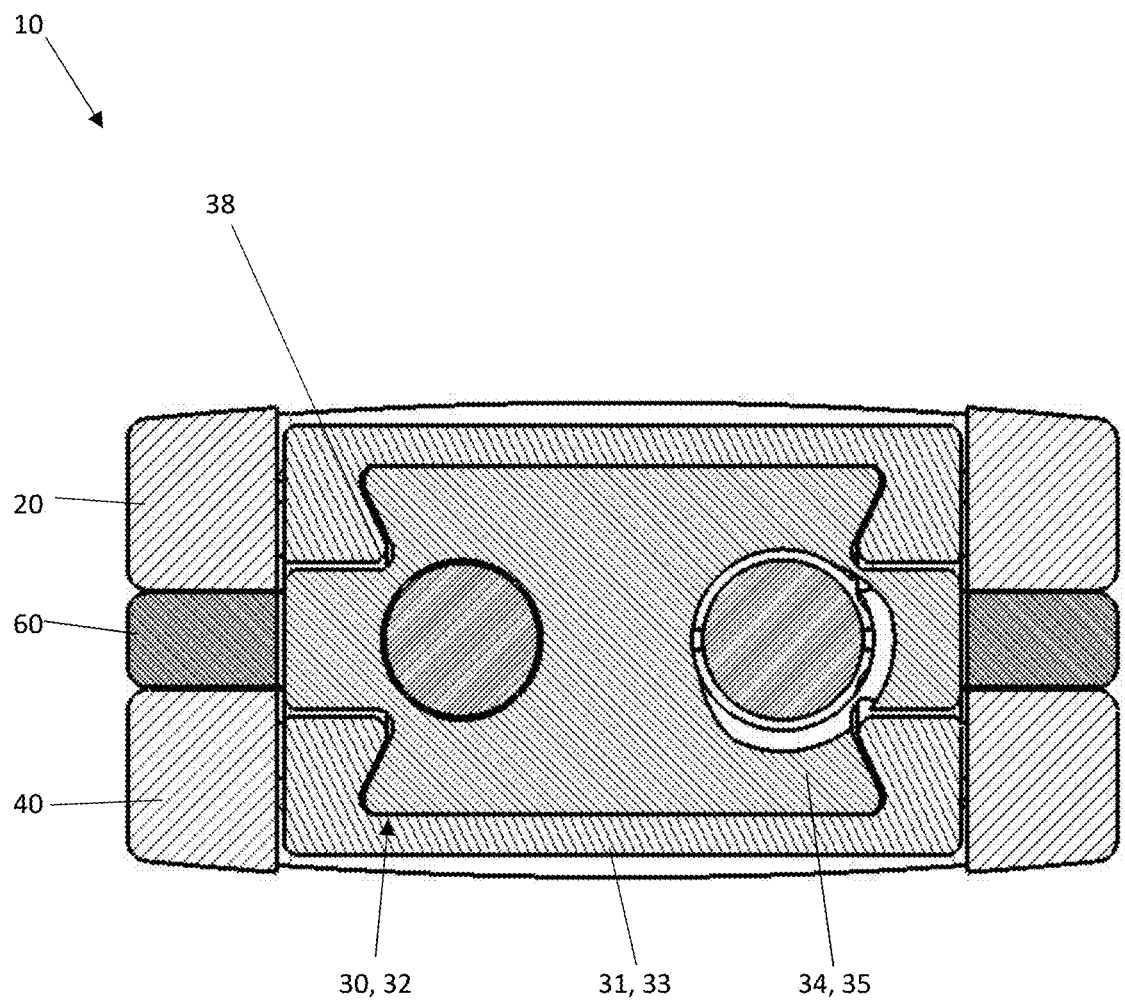
FIG. 11A is a right cross-sectional view of the device of the present invention in a contracted position at the ramp dovetail feature.
Figure 11B:
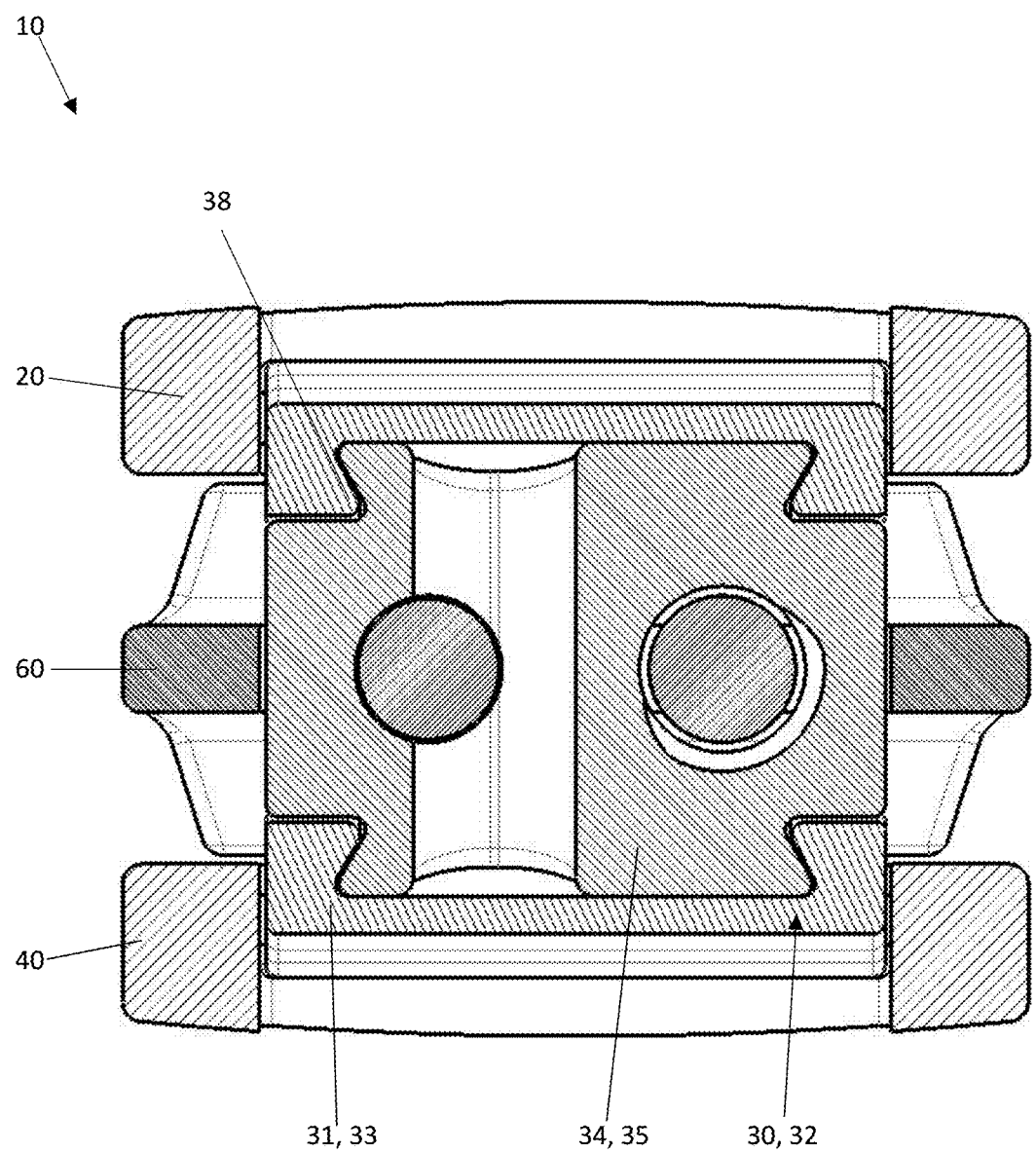
FIG. 11B is a right cross-sectional view of the device of the present invention in an expanded position at the ramp dovetail feature.

With reference to FIGS. 11A and 11B, cross sectional views of the ramp assemblies 30, 32 are shown contained in the frame 60 and base plates 20, 40. In FIG. 11A, the implant device 10 is shown in a fully contracted position, when this occurs, the implant device 10 shows the pivoting hinged ramps 31, 33 with the groove 38 shown as a dovetail feature that interlocks the lateral sides of the pivoting hinged ramps 31, 33 projecting inwardly the dovetail or groove 38 of the translating ramp 34, 35 as illustrated. When this occurs, it locks the ramp from moving laterally. As shown, this prevents the pivoting hinged ramps 31, 33 from laterally shifting when the device 10 is in the expanded position, furthermore, the base plates 20, 40 further provide a constraint on movement of the translating ramps 34, 35 to which the pivoting hinged ramps 31, 33 are attached. With reference to FIG. 11B, the pivoting hinged ramp 31, 33 is shown in the elevated or expanded position, an important aspect of the present invention as illustrated is that even in the fully expanded position, it is noticed that the pivoting hinged ramps 31, 33 are fully supported on both sides by the translating ramps 34, 35. This provides lateral stability for the base plates 20, 40 that are hinged to the pivoting hinged ramps 31, 33 on each lateral side. This means that the rigidity of the device 10 is extremely secure and the device 10 is unlikely to flex or twist.

Figure 12:
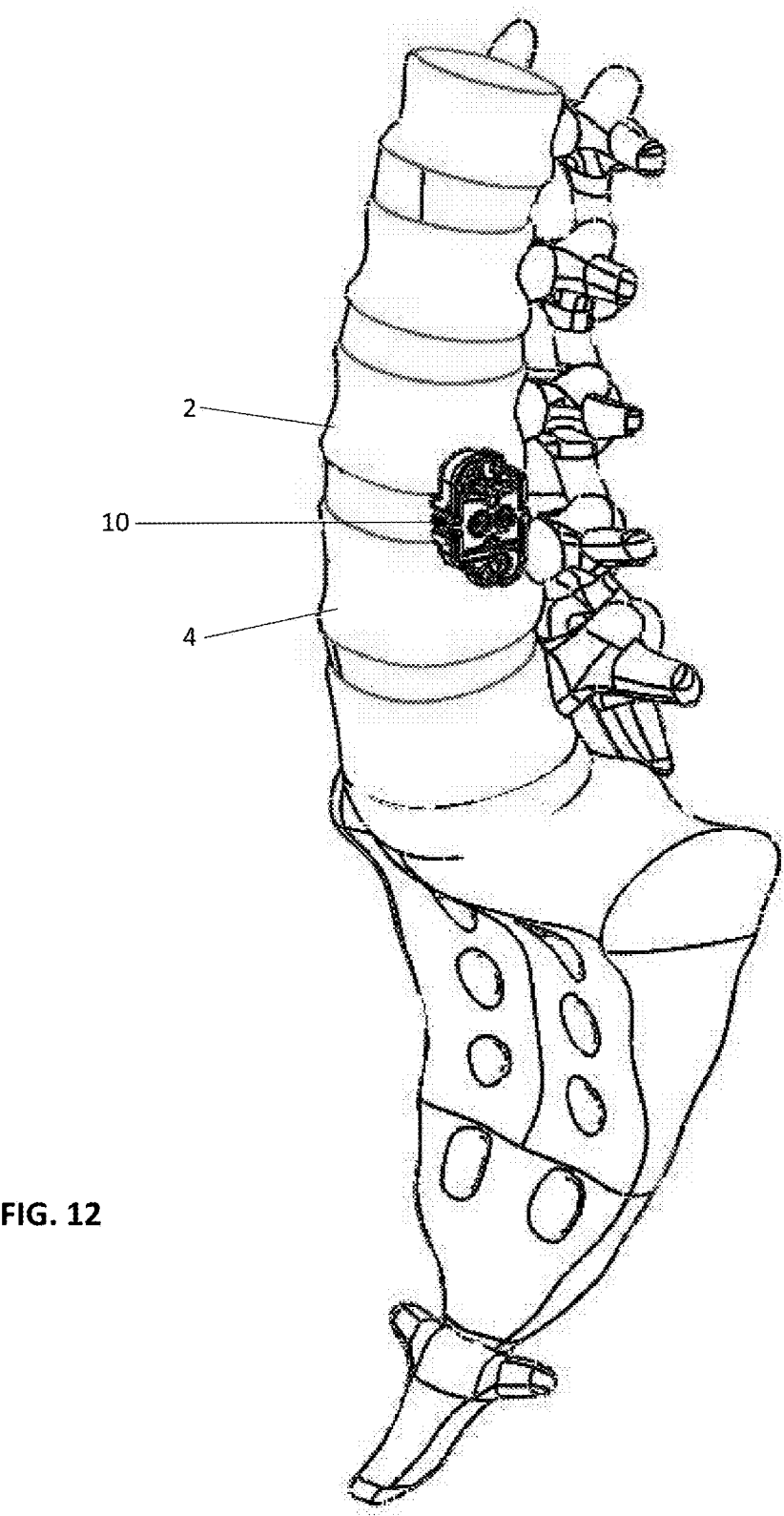
FIG. 12 is a perspective view of the implant device of the present invention shown implanted between two vertebral bodies of a spine.
Figure 13:
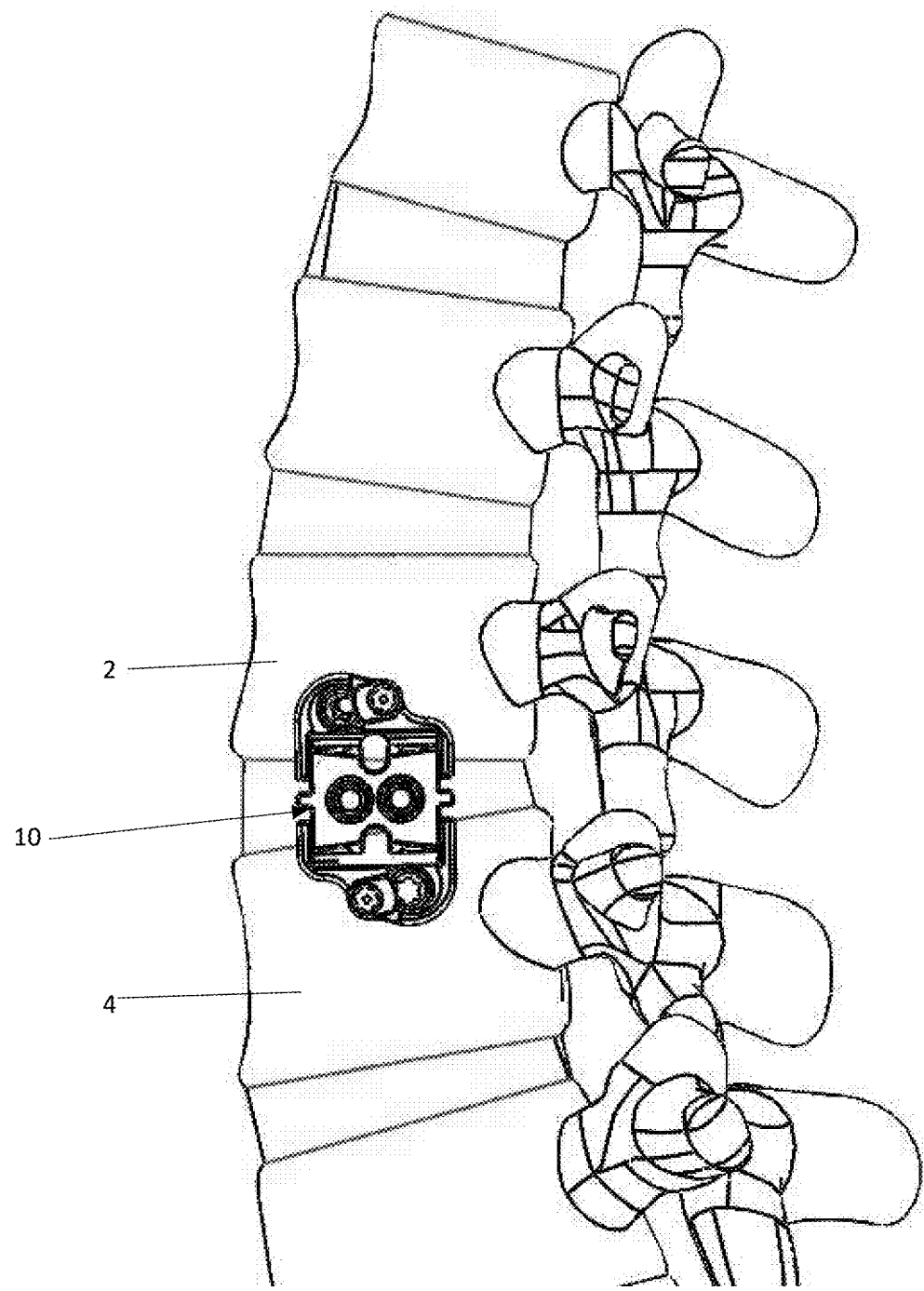
FIG. 13 is a front view taken from FIG. 12 of the implant device of the present invention shown implanted between two vertebral bodies of a spine.
Figure 14:
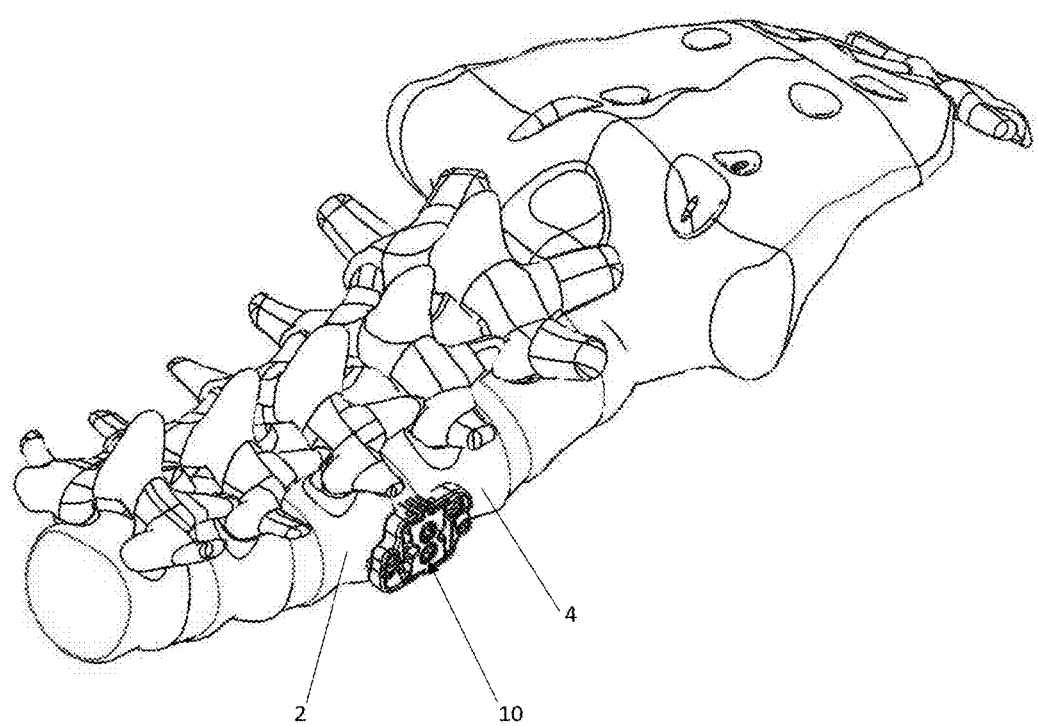
FIG. 14 is a perspective view of the implant device of the present invention shown implanted between two vertebral bodies of a spine.
Figure 15:
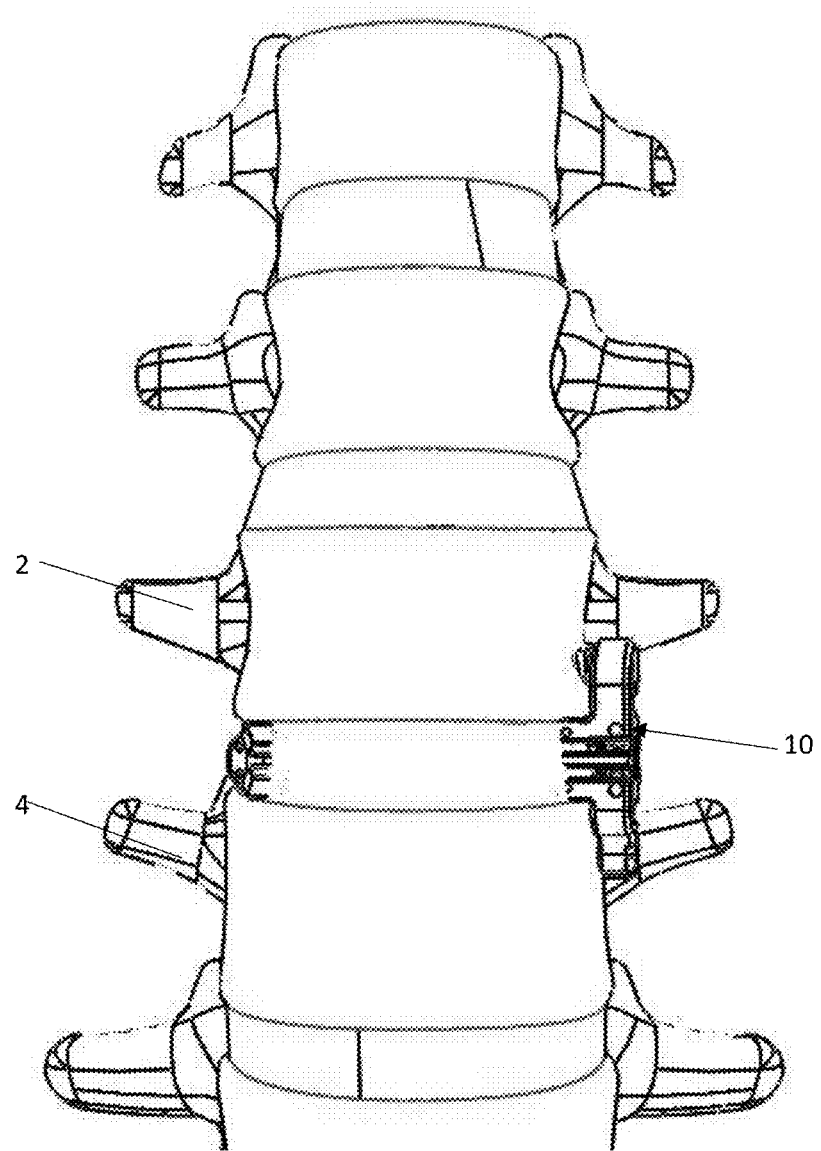
FIG. 15 is a side view taken from FIG. 12 of the implant device of the present invention shown implanted between two vertebral bodies of a spine.

With reference to FIGS. 12-15, the implant device 10 is shown inserted between two adjacent vertebral bodies 2, 4 on implantation. As illustrated in FIGS. 12 and 13, it is clearly shown how the device 10 will be implanted. FIG. 14, similarly shows a different perspective view of the implanted device 10. FIG. 15, on a head-on view, shows that most of the device 10 is hidden by the disc space when inserted in between the vertebral bodies 2, 4.

An important aspect of the present invention although not fully discussed is best seen in the top views. With reference to FIGS. 10A-10B, top views of the implant device 10 are illustrated, it is important to understand that the top and bottom views are virtually identical and that the base plates 20, 40 provide a perimeter frame with a large opening or aperture 12. When the device 10 is in the expanded position either proximally or distally one of the translating ramps 34, 34 will move making the aperture or opening space 12 between the base plates 20, 40 extremely large. When both translating ramps 34, 35 are moved into the expanded position this aperture space is increased even further. This provides for a large amount of space for allograft material or other biologics to be placed inside the implant device 10 to enhance the osteoinductive effect of new bone growth which is extremely important in any fusion device. It is believed that this capability is best achieved by the drive mechanisms used that are independently driven by the mechanism of this implant device according to the present invention.

While the present invention has been shown with endplates 21, 41, these end plates could be removed and the implant device 10 would no longer be a standalone device which can be inserted and then fastened directly into the vertebral bodies, but may have a separate vertebral plate that can be added if these end plates are not provided. These optional features, when provided, show the best mode of practicing the invention. However, they are not necessary for utilization of the device 10 according to the present invention.

Figure 16:
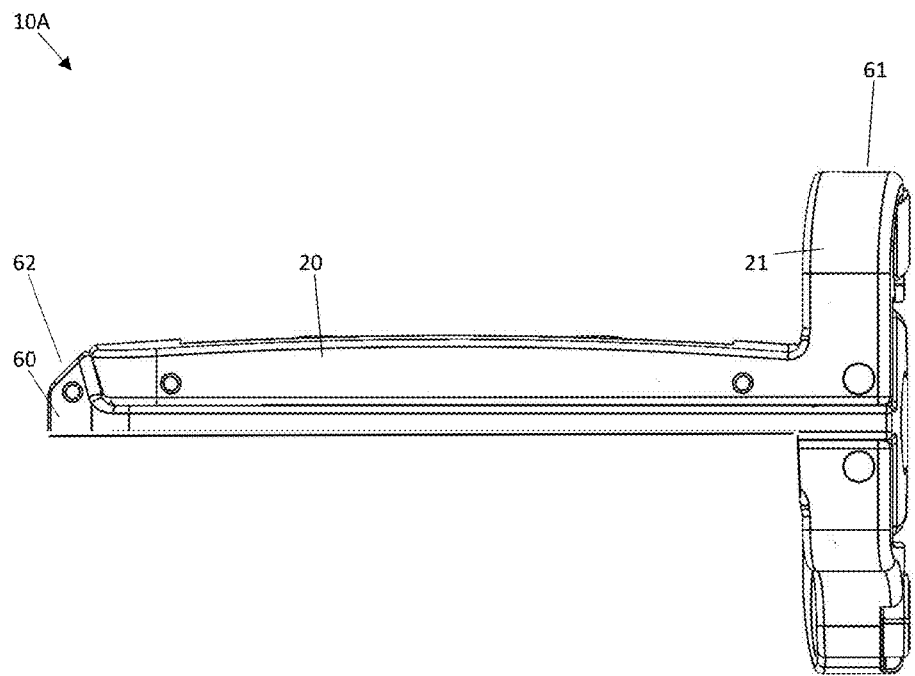
FIG. 16 is a side view of a first alternative embodiment showing the device made with one base plate and a frame.

The preferred device 10 is shown where the base plates are provided on both an upper and a lower surface. Also, as a first alternative embodiment, device 10A, it is understood that one base plate could be provided only and that the frame itself would be a stationary base plate. In such a condition either the base plate 20 or base plate 40 could be removed and only one provided, as shown in FIG. 16. Furthermore, it is understood that the angular inclination of the device 10, 10A is only limited by the maximum height that the device can be expanded. The device is only limited by the shape and contours of the ramps. As noted, the ramps have a radius contour or curved contour such that it increases rapidly at initial movement from a contracted position and this rate of movement changes as the ramp achieves the peak of the curvature. This provides for very fine tuning and adjustment by the surgeon as he approaches a maximum condition and a larger range of height adjustment with a constant bearing surface area for increased stability at all expanded heights. It is further understood that any inclination between contracted and fully expanded can be established by simply stopping the rotation of the drive shaft. The drive shaft will maintain its position regardless of where it is stopped. Therefore, the surgeon can pick precisely the location he wants to elevate the proximal or distal end independent of the other such that any inclination can be achieved with the range of that provided by the threads on the ramp and drive shaft and the contour surface of the ramps themselves. These and other variations can be achieved by the present device which is believed unique over all expandable implant devices currently in use.

The present invention can be made in a variety of sizes, by way of example, widths: 18 mm and 22 mm; longitudinal lengths: 40, 45, 50, 55, and 60 mm; Distal and Proximal end height: 8 mm; Center height range: 9 mm (contracted)-15 mm (expanded); Maximum distal or proximal angle: 40 mm length: 10°; 45 mm length: 9°; 50 mm length: 8°; 55 mm length: 7°; 60 mm length: 6°.

Figure 17A:
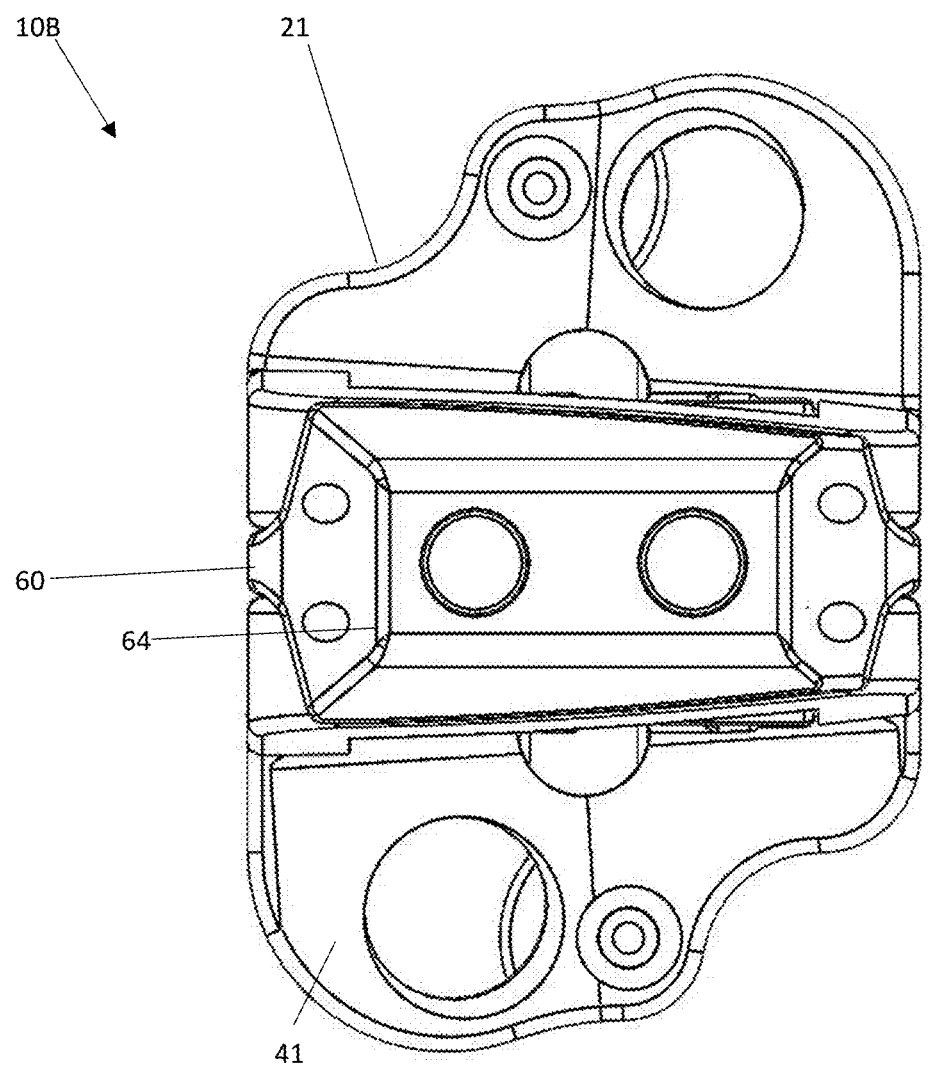
FIG. 17A is an end view of a second alternative of the present invention having a laterally inclined outer surface of the base plates configured to mimic a lordotic curvature at a first lordotic angle less than or equal to 10 degrees.
Figure 17B:
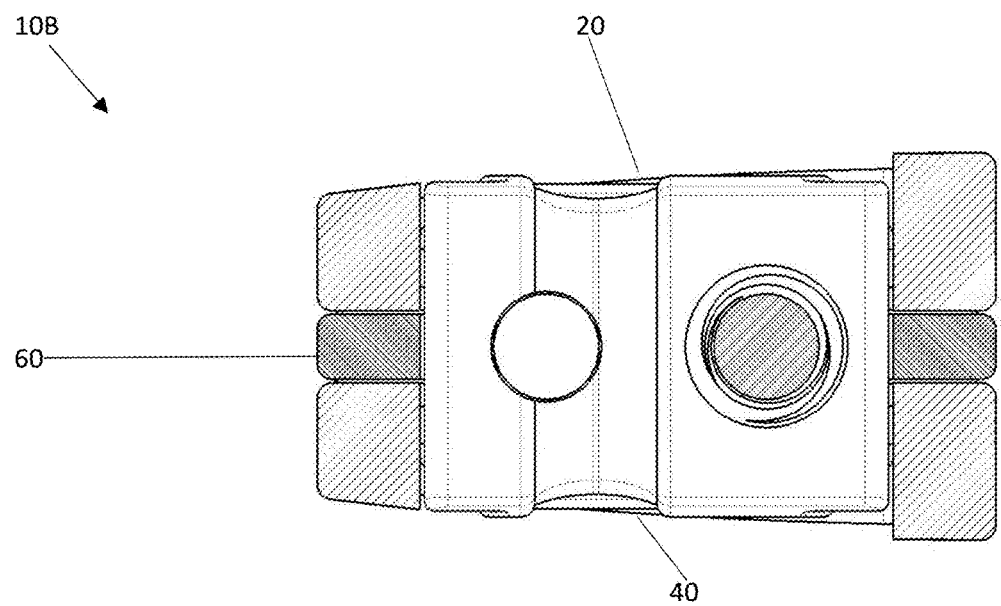
FIG. 17B is a right section view of the second embodiment of FIG. 17A.
Figure 18A:
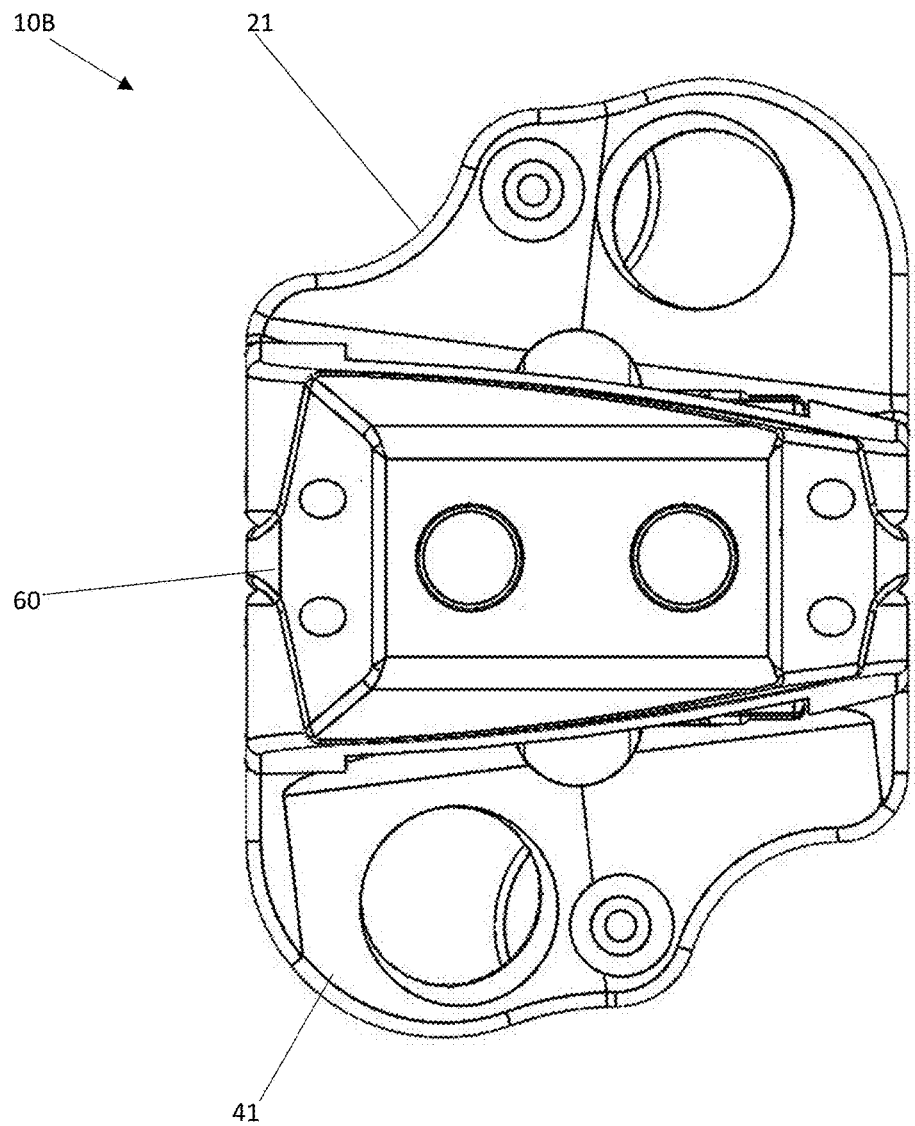
FIG. 18A is an end view of a second alternative of the present invention having a laterally inclined outer surface of the base plates configured to mimic a lordotic curvature at a first lordotic angle greater than 10 degrees.
Figure 18B:
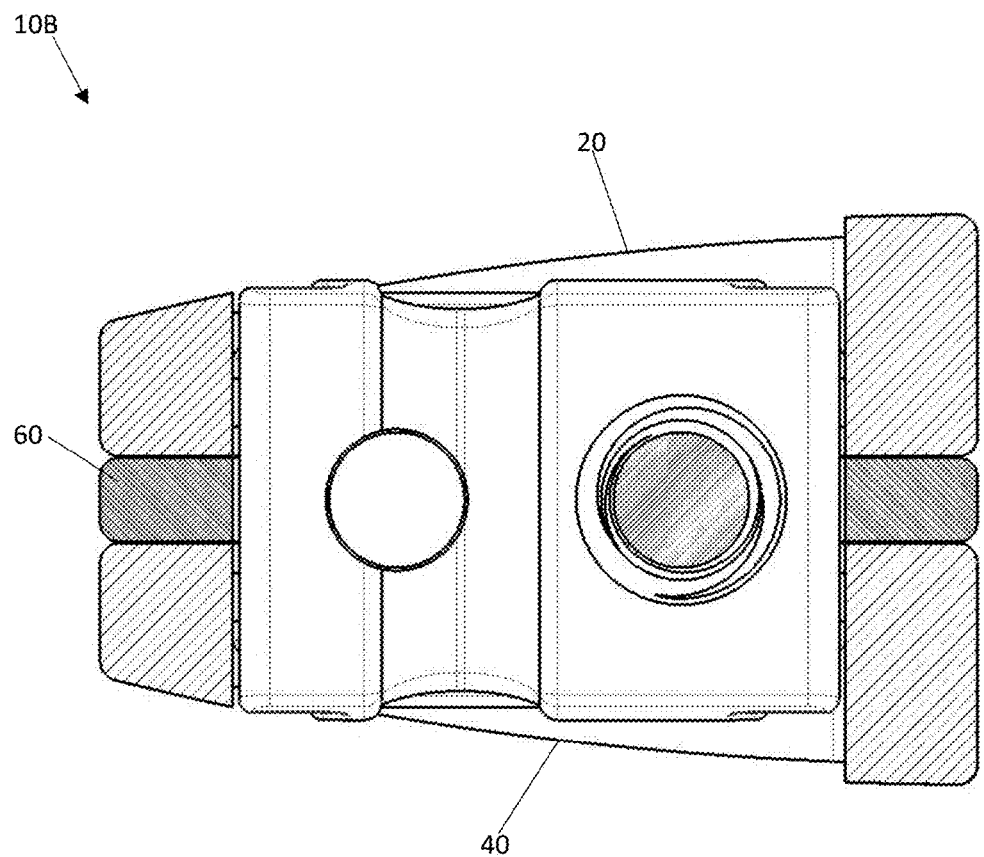
FIG. 18B is a right section view of the second embodiment of FIG. 18A.
Figure 19A:
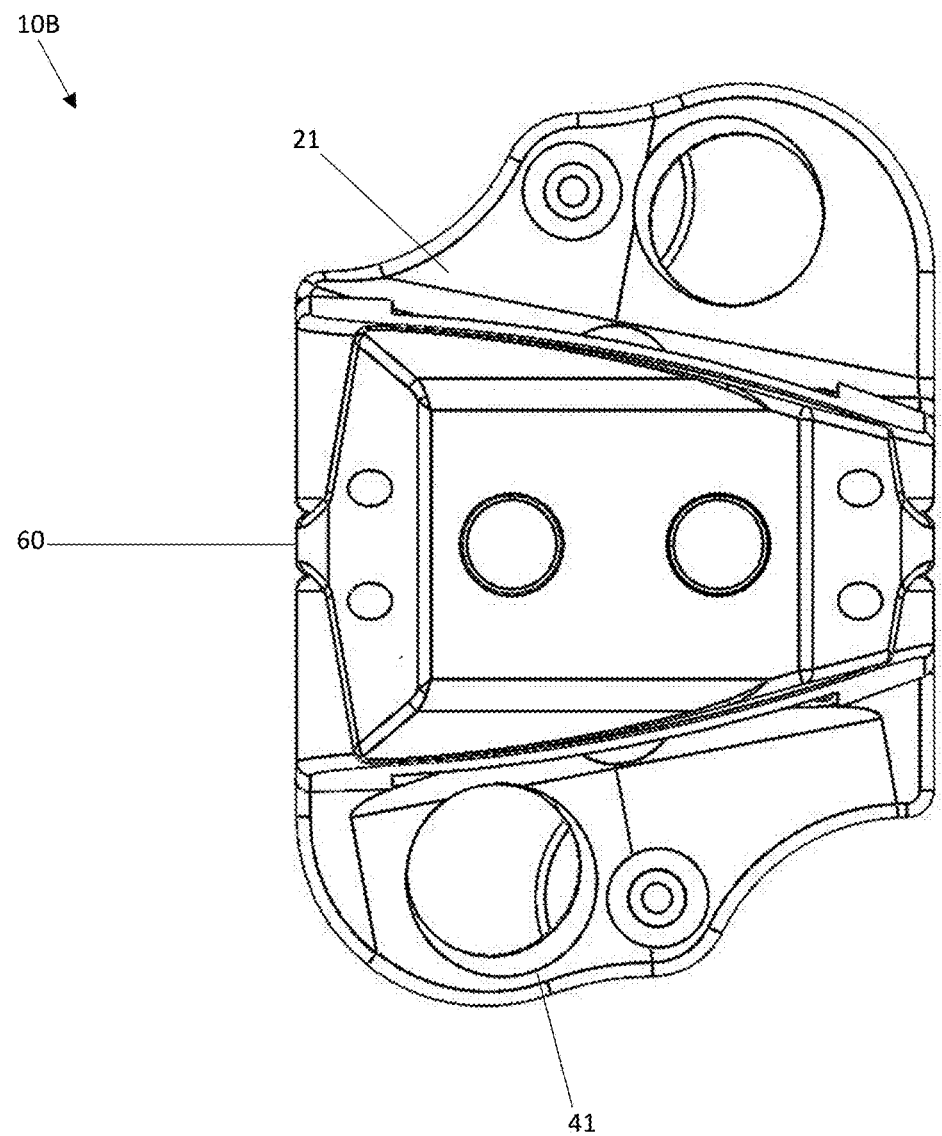
FIG. 19A is an end view of a second alternative of the present invention having a laterally inclined outer surface of the base plates configured to mimic a lordotic curvature at a first lordotic angle greater than 15 degrees.
Figure 19B:
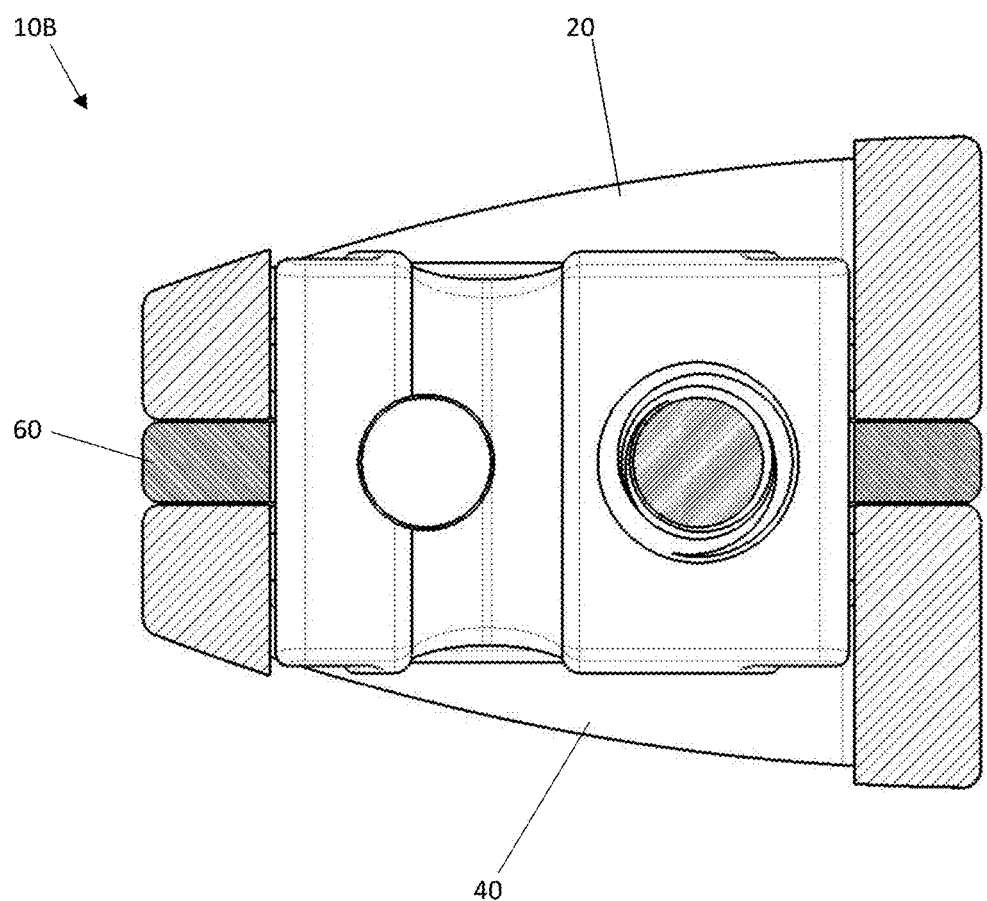
FIG. 19B is a right section view of the second embodiment of FIG. 19A.

With reference to FIGS. 17A-19B, a second alternative embodiment 10B is shown having a laterally inclined outer surface of the base plates 20, 40 configured to mimic a lordotic curvature of the lumbar spine. FIGS. 17A-17B illustrate a 7° Lordosis-Anterior (tall side) height range: 10 mm-16 mm FIGS. 18A-18B illustrate a 14° Lordosis-Anterior (tall side) height range: 12 mm-18 mm FIGS. 19A-19B illustrate a 21° Lordosis-Anterior (tall side) height range: 14 mm-20 mm. The effective angles are achieved by changing the thickness of the left or anterior side of the base plates relative to the right side of the base plates.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An expandable interbody fusion implant device comprises:
    a frame having a distal end and a proximal end;
    a distal ramp assembly and a proximal ramp assembly, each ramp assembly having a translating ramp, a first pivoting hinged ramp and a second pivoting hinged ramp;
    a first base plate overlying a second base plate, the base plates disposed between the distal end and the proximal end of the frame, each base plate being hinged to the distal ramp assembly and the proximal ramp assembly at an end of one of said pivoting hinged ramps of each ramp assembly;
    each translating ramp comprising an exterior lift surface having a convex curvature contoured to guide and support the pivoting hinged ramps during expansion or contraction of the base plates, each pivoting hinged ramp comprising a contoured support surface having a concave curvature complimentary to the exterior lift surface configured to slide on the exterior lift surface of the translating ramps;
    two independently driven drive shafts, the two independently driven drive shafts comprising a first drive shaft for translating the distal ramp assembly and a second drive shaft for translating the proximal ramp assembly, each drive shaft being affixed to the frame at the distal and proximal ends; and
    wherein rotation of the first drive shaft can independently drive the distal ramp assembly to selectively expand or contract a distance between the two base plates distally, rotation of the second drive shaft can independently drive the proximal ramp assembly to selectively expand or contract a distance between the two base plates proximally and sequential or simultaneous rotation of both first and second drive shafts independently drives the distal and proximal ramps to selectively expand or contract a distance between both first and second base plates relative to the frame.

2. The expandable interbody fusion implant device of claim 1 wherein during distal expansion of the base plates the distal ramp assembly moves directionally toward the distal end of the frame on rotation of the first drive shaft.

3. The expandable interbody fusion implant device of claim 1 wherein during proximal expansion of the base plates the proximal ramp assembly moves directionally toward the proximal end of the frame on rotation of the second drive shaft.

4. The expandable interbody fusion implant device of claim 1 wherein each translating ramp has a stop wall configured to stop the pivoting hinged ramps at a full expansion height on both the distal and proximal ramp assemblies.

5. The expandable interbody fusion implant device of claim 1 wherein the exterior lift surface of each translating ramp has a radius of curvature of decreasing inclination toward a center of the frame of the device and of increasing inclination toward ends of the frame configured to initially rapidly expand or contract near a collapsed or retracted position and a slower expansion or contraction near a fully expanded position configured to allow a larger range of height adjustment with a constant bearing surface area for increased stability of all expanded heights.

6. The expandable interbody fusion implant device of claim 1 wherein each translating ramp has a pair of opposing sides, each side has a pair of guide channels or grooves, at least one of the pair of guide channels or grooves configured for receiving and guiding one of the pivoting hinged ramps, wherein each pivoting hinged ramp has a lateral side keyed into the guide channel or groove wherein each guide channel or groove has an end to limit the expansion of the pivoting hinged ramp.

7. The expandable interbody fusion implant device of claim 1 wherein the distal end of the frame has a tapered end configured to facilitate insertion between vertebral bodies.

8. The expandable interbody fusion implant device of claim 1 wherein the proximal end of the frame has a first opening and a second opening for receiving the first and second drive shafts, respectively, and further has lateral sides with slotted channels to receive a pin fixed to the proximal end of each of the first and second base plates, the pins configured to allow the base plates to slide relative to the proximal end of the frame during expansion or contraction.

9. The expandable interbody fusion implant device of claim 8 wherein the first and second base plates each have at the proximal end an end plate with a fastener opening for securing the implant to a vertebral body, each end plate being integral to and selectively movable with the base plate during expansion or contraction.

10. The expandable interbody fusion implant device of claim 9 wherein each end plate further has a locking tab attached to the end plate, the locking tab being rotatable to cover a portion of a fastener from loosening after being affixed to a vertebral body.

* * * * *